(12) United States Patent
Morris et al.

(10) Patent No.: US 8,491,884 B2
(45) Date of Patent: *Jul. 23, 2013

(54) VIRUS CLEARANCE OF NEOPLASTIC CELLS FROM MIXED CELLULAR COMPOSITIONS

(75) Inventors: Donald Morris, Calgary (CA); Bradley G. Thompson, Calgary (CA); Matthew C. Coffey, Calgary (CA)

(73) Assignee: Oncolytics Biotech Inc., Calgary Alberta (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/080,856

(22) Filed: Apr. 6, 2011

(65) Prior Publication Data

US 2011/0200565 A1 Aug. 18, 2011

Related U.S. Application Data

(60) Continuation-in-part of application No. 12/652,289, filed on Jan. 5, 2010, which is a continuation of application No. 11/807,771, filed on May 30, 2007, which is a continuation of application No. 10/602,024, filed on Jun. 24, 2003, now Pat. No. 7,306,902, said application No. 12/652,289 is a continuation-in-part of application No. 10/931,728, filed on Aug. 31, 2004, now abandoned, which is a division of application No. 09/847,355, filed on May 3, 2001, now abandoned, application No. 13/080,856, which is a continuation of application No. 11/807,921, filed on May 30, 2007, now abandoned, which is a continuation of application No. 10/931,728, which is a division of application No. 09/847,355.

(60) Provisional application No. 60/392,031, filed on Jun. 28, 2002, provisional application No. 60/443,188, filed on Jan. 29, 2003, provisional application No. 60/276,782, filed on Mar. 16, 2001, provisional application No. 60/268,054, filed on Feb. 13, 2001, provisional application No. 60/205,389, filed on May 19, 2000, provisional application No. 60/201,990, filed on May 3, 2000.

(51) Int. Cl.
*A61K 51/00* (2006.01)
*A61K 48/00* (2006.01)

(52) U.S. Cl.
USPC .................................. 424/93.2; 424/232.1

(58) Field of Classification Search
None
See application file for complete search history.

(56) References Cited

U.S. PATENT DOCUMENTS

| | | |
|---|---|---|
| 4,576,928 A | 3/1986 | Tani et al. |
| 5,514,340 A | 5/1996 | Lansdorp et al. |
| 5,585,096 A | 12/1996 | Martuza et al. |
| 5,670,330 A | 9/1997 | Sonenberg et al. |
| 5,801,029 A | 9/1998 | McCormick |
| 5,837,512 A | 11/1998 | Rabson et al. |
| 5,840,502 A | 11/1998 | Van Vlasselaer |
| 5,861,159 A | 1/1999 | Pardoll et al. |
| 6,136,307 A | 10/2000 | Lee et al. |
| 6,475,481 B2 | 11/2002 | Talmadge |
| 6,528,057 B1 | 3/2003 | Ambrus et al. |
| 6,596,268 B1 * | 7/2003 | Coffey et al. ............ 424/93.2 |
| 6,649,157 B2 | 11/2003 | Coffey et al. |
| 6,777,177 B1 | 8/2004 | Rubin et al. |
| 6,994,858 B2 | 2/2006 | Morris et al. |
| 7,192,580 B2 * | 3/2007 | Atkins et al. ............ 424/93.2 |
| 7,252,817 B2 * | 8/2007 | Coffey et al. ............ 424/93.1 |
| 7,306,902 B2 | 12/2007 | Thompson et al. |
| 7,731,951 B2 * | 6/2010 | Coffey et al. ............ 424/93.1 |
| 7,780,962 B2 | 8/2010 | Roberts et al. |
| 2001/0048919 A1 | 12/2001 | Morris et al. |
| 2002/0037543 A1 | 3/2002 | Atkins et al. |
| 2003/0044384 A1 | 3/2003 | Roberts et al. |
| 2003/0138405 A1 | 7/2003 | Fueyo et al. |

FOREIGN PATENT DOCUMENTS

| | | |
|---|---|---|
| CA | 2283280 | 2/1999 |
| CA | 2508238 | 2/1999 |
| EP | 0451611 | 10/1991 |
| EP | 0931830 | 7/1999 |
| EP | 1344819 | 9/2003 |
| WO | WO94/18992 | 9/1994 |
| WO | WO94/25627 | 11/1994 |
| WO | WO99/08692 | 2/1999 |
| WO | WO99/18799 | 4/1999 |
| WO | WO99/45783 | 9/1999 |
| WO | WO00/50051 | 8/2000 |
| WO | WO00/62735 | 10/2000 |
| WO | WO01/19380 | 3/2001 |

(Continued)

OTHER PUBLICATIONS

Thorne, Steve et al. Journal of Clinical Investigation (2007), 117(11), pp. 3350-3358.*

(Continued)

*Primary Examiner* — Bao Li
(74) *Attorney, Agent, or Firm* — Kilpatrick, Townsend & Stockton, LLP

(57) ABSTRACT

The present invention relates to a method for removing neoplastic cells from a mixed cellular composition, which is outside of a living organism, by using a virus which selectively infect and kill neoplastic cell. A variety of viruses can be used in this method to remove neoplastic cells for different purposes, for example, to purge hematopoietic stem cells prior to transplantation. Also provided are compositions prepared according to this method, and kits comprising a combination of viruses which are useful in this invention.

44 Claims, 16 Drawing Sheets

FOREIGN PATENT DOCUMENTS

| | | |
|---|---|---|
| WO | WO01/35970 | 5/2001 |
| WO | WO01/37866 | 5/2001 |
| WO | WO01/83710 | 11/2001 |
| WO | WO02/04596 | 1/2002 |
| WO | WO02/39117 | 5/2002 |

OTHER PUBLICATIONS

Adachi et al., A midkine promoter-based conditionally replicative adenovirus for treatment of pediatric solid tumors and bone marrow tumor purging, Cancer Research, 61:7882-7888 (2001).
Andreansky et al., Evaluation of genetically engineered herpes simplex viruses as oncolytic agents for human malignant brain tumors, Cancer Research, 57:1502-9 (1997).
Armstrong et al., Studies on reovirus receptors of L cells: virus binding characteristics and comparison with reovirus receptors of erythrocytes, Virology, 138(1):37-48 (1984).
Bar-Eli et al., Preferential cytotoxic effect of Newcastle disease virus on lymphoma cells, J. Cancer Res. Clin. Oncol., 122(7):409-415 (1996).
Bashey et al., Proliferative but not nonproliferative responses to granulocyte colony-stimulating factor are associated with rapid activation of the p21rasIMAP kinase signalling pathway, Blood, 83(4):949-957 (1994).
Bensinger, Should we purge? Bone Marrow Transplant, 21(2):113-115 (1998).
Bischoff et al., An adenovirus mutant that replicates selectively in p53-deficient human tumor, Science, 274 (5286):373-376 (1996).
Blagosklonny et al., In vitro evaluation of a p53-expressing adenovirus as an anti-cancer drug, Int. J. Cancer, 67 (3):386-392 (1996).
BOS, Ras oncogenes in human cancer: a review, Cancer Res., 49(17):4682-4689 (1989).
Campbell et al., Increasing complexity of ras signaling, Oncogene, 17:1395-1413 (1998).
Chandran et al., Protease cleavage of reovirus capsid protein mu1 and mu1C is blocked by alkyl sulfate detergents, yielding a new type of infectious sub virion particle, J. Virol., 72(1):467-475 (1998).
Chang et al., Rescue of vaccinia virus lacking the E3L gene by mutants of E3L, J. Virol., 69(10):6605-6608 (1995).
Chang et al., Identification of a conserved motif that is necessary for binding of the vaccinia virus E3L gene products to double-stranded RNA, Virology, 194(2):537-547 (1993).
Chang et al., The E3L gene of vaccinia virus encodes an inhibitor of the interferon-induced, double-stranded RNA-dependent protein kinase. Proc. Nat. Acad. Sci., 89(11):4825-4829 (1992).
Coffey et al., Reovirus therapy of tumors with activated ras pathway, Science, 282(5392):1332-1334 (1998).
Coukos et al., Multi-attenuated herpes simplex virus• 1 mutant G207 exerts cytotoxicity against epithelial ovarian cancer but not normal mesothelium and is suitable for intraperitoneal oncolytic therapy, Cancer Gene Therapy,7:275-283 (2000).
Cozzi et al., Xenotransplantation, where do we stand? J. Nephrology, 16(7):S16-S21 (2003).
Duggan et al., Predictive factors for long-term engraftment of autologous blood stem cells, Bone Marrow Transplant, 26(12):1299-1304 (2000).
Duman et al., Successful treatment of post-transplant Kaposi's sarcoma by reduction of immunosuppression, Nephrol. Dial. Transplant, 17:892-896 (2002).
Einspahr et al., Association of ki-ras proto-oncogene mutation and p53 gene overexpression in sporadic colorectal adenomas with demographic and clinicopathologic characteristics, Cancer Epidemiol. Biomarkers Prev., 15 (8):1443-1450 (2006).
Ezzat et al., An overview of breast cancer, Annals of Saudi Medicine, 17(1):10-15 (1997).
Freshney, Culture of animal cells: a manual of basic technique, Second Edition, p. 217 (1997).
Fueyo et al., A mutant oncolytic adenovirus targeting the Rb pathway produces anti-glioma effect in vivo, Oncogene, 19(1):2-12 (2000).

Gao et al., Rapid in situ hybridization technique for detecting malignant mouse cell contamination in human xenograft tissue from nude mice and in vitro cultures from such xenografts, Prostate, 39(1):67-70 (1999).
Garcia-Castro et al., Purging of leukemia-contaminated bone marrow grafts using suicide adenoviral vectors: an in vivo murine experimental model, Gene Therapy,10:1328-1335 (2003).
Gariglio et al., Inhibition of interferon-gamma antiviral and antiproliferative activities by ras oncogene expression, J. of Nat. Cancer Institute, 81:1014-1020 (1989).
Gentsch et al., Effect of neuraminidase treatment of cells and effect of soluble glycoproteins on type 3 reovirus attachment to murine L cells, J. Virol., 56(2):356-364 (1985).
Graham et al., Varying degrees of amplification of the N-ras oncogene in the human breast cancer cell line MCF-7, Cancer Research, 45:2201-2205 (1985).
Gulati et al., Rationale for purging in autologous stem cell transplantation, J. Hematother., 2(4):467-471 (1993).
Gutkind, The Pathways connecting G protein-coupled receptors to the nucleus through divergent mitogen-activated protein kinase cascades, J. Biol. Chem.,273:1839-1842 (1998).
Haig et al., The orf virus OV20.0L gene product is involved in interferon resistance AV and inhibits an interferon-inducible, double-stranded RNA-dependent kinase, Immunology, 93(3):355-340 (1998).
Hashiro et al., The preferential cytotoxicity of :reovirus for certain transformed cell lines, Archives of Virology, 54:307-315 (1977).
He et al., The gamma(1)34.5 protein of herpes simplex virus 1 complexes with protein phosphatase 1α to dephosphorylate the α subunit of the eukaryotic translation initiation factor 2 and preclude the shutoff of protein synthesis by double-stranded RNA-activated protein kinase, Proc. Nat. Acad. Sci., 94:843-848 (1997).
Hirai et al., Adenovirus p53 purging for human breast cancer stem cell products, Acta Haematol., 101(2):97-105 (1999).
Hirasawa et al., Oncolytic reovirus against ovarian and colon cancer, Cancer Research, 622:1696-1701 (2002).
Janes et al., Activation of the Ras signalling pathway in human breast cancer cells overexpressing erbB-2, Oncogene, 9(12):3601-3608 (1994).
Kawagishi-Kobayashi et al., Regulation of the protein kinase PKR by the vaccinia virus pseudosubstrate inhibitor K3L is dependent on residues conserved between the K3L protein and the PKR substrate eIF2α, Mol. Cell. Biology, 17 (7):4146-4158 (1997).
Kennedy et al., High-dose chemotherapy with reinfusion of purged autologous bone marrow following dose-intense induction as initial therapy for metastatic breast cancer, J. Natl. Cancer Inst., 83(13):920-926 (1991).
Kozma et al., The human c-kirsten ras gene is activated by a novel mutation in codon 13 in the breast carcinoma cell line MDA-MB231, Nucleic Acids Research, 15(15):5963-5971 (1987).
Lambright et al., Effect of pre-existing anti-herpes immunity on the efficacy of herpes simplex viral therapy in a murine intraperitoneal tumor model, Mol. Ther., 2(4):387-393 (2000).
Lichty et al., Identification of vesicular stomatitis virus as a leukemolytic agent, Blood, 96(11):213b (2000) (Abstract).
Lillo et al., Efficient and nontoxic adenoviral purging method for autologous transplantation in breast cancer patients, Cancer Research, 62:5013-5018 (2002).
Lorence et al., Newcastle disease virus as an antineoplastic agent: induction of tumor necrosis factor-alpha and augmentation of its cytotoxicity, J. Natl. Cancer Inst., 80:1305-1312 (1998).
Marini et al., Purging of contaminating breast cancer cells from hematopoietic stem cell grafts by adenoviral GAL-TEK gene therapy and magnetic antibody cell separation, Clin. Cancer Res., 5(6):1557-1568 (1999).
Nemunaitis, Oncolytic viruses, Invest. New Drugs, 17(4):375-386 (1999).
Nibert et al., Reoviruses and their replication, pp. 1557-1596 in Virology (Fields et al, 3rd Edition), Lippencott-Raven Press (1996).
Nielsen et al., P53 tumor suppressor gene therapy for cancer, Cancer Gene Ther., 5(1):52-63 (1998).
Nieto et al., Autologous stem-cell transplantation for solid tumors in adults, Hematol. Oncol. Clin.. North Am., 13 (5):939-968 (1999).

Nordon et al., Ex vivo manipulation of cell subsets for cell therapies, Artif. Organs, 20(5):396-402 (1996).

Norman et al., Reovirus oncolysis: The ras/RalGEF/p38 pathway dictates host cell permissiveness to reovirus infection, Proc. Nat. Acad. Sci., 101(930):11099-11104 (2004).

Norman et al., Reovirus oncolysis of human breast cancer, Human Gene Therapy, 13(5):641-652 (2002).

Norman et al., Reovirus as a novel oncolytic agent, J. Clin. Invest., 105(8):1035-1038 (2000).

O'Reilly, Allogenic bone marrow transplantation: current status and future directions, J. Amer. Soc. Hematology, 62 (5) 941-964 (1983).

Paul et al., The-anomeric form of sialic acid is the minimal receptor determinant recognized by reovirus, Virology, 172(1):382-385 (1989).

Portella et al., ONYX-015, an E1B gene defective adenovirus, induces cell death in human anaplastic thyroid carcinoma cell lines, J. Clinical Endocrinology & Metabolism, 87(6):2525-31 (2002).

Rausch et al., Cooperation of p38 and extracellular signal-regulated kinase mitogen-activated protein kinase pathways during granulocyte colony-stimulating factor-induced hemopoietic cell proliferation, J. Biol. Chem., 274 (7):4096-4105 (1999).

Reddy, Mobilization and collection of peripheral blood progenitor cells for transplantation, Transfus. Apher. Sci., 32 (1):63-72 (2005).

Reichard et al., Newcastle disease virus selectively kills human tumor cells, J. of Surgical Research, 52(5):448-453 (1992).

Ring, Cytolytic viruses as potential anti-cancer agents, J. General Virology, 83:491-502 (2002).

Romano et al., Inhibition of double-stranded RNA-dependent protein kinase PKR by vaccinia virus E3: role of complex formation and the E3 N-terminal domain, Mol. Cell. Biol.,18(12):7304-7316 (1998).

Satoh et al., Involvement of ras p21 protein in signal-transduction pathways from interleukin 2, interleukin 3, and granulocyte/macrophage colony-stimulating factor, but not from '-inter1eukin 4, Proc. Natl. Acad. Sci. USA, 88 (8):3314-3318 (1991).

Seth et al., Adenovirus-mediated gene transfer to human breast tumor cells: an approach for cancer gene therapy and bone marrow purging, Cancer Research, 56(6):1346-1351 (1996).

Sharp et al., The vaccinia virus E3L gene product interacts with both the regulatory and the substrate binding regions of PKR: implications for PKR autoregulation, Virol., 250(2):302-315 (1998).

Shpall et al., A prospective randomized trial of buffy coat versus CD34-selected autologous bone marrow support in high-risk breast cancer patients receiving high-dose chemotherapy, Blood, 90(11):4313-4320 (1997).

Smith et al., Correlations among p53, Her-2 1neu, and ras overexpression and aneuploidy by multiparameter flow cytometryin human breast cancer: evidence for a common phenotypic evolutionary pattern in infiltrating ductal carcinomas, Clin. Cancer Res., 6(1):112-26 (2000).

Smith et al., Oncolytic viruses and tumors: turning one scourge against another, Expert Opin. Investig. Drugs, 9 (2):311-27 (2000).

Smith et al., Polypeptide components of virions, top component and cores of reovirus type 3, Virology, 39:791-800 (1969).

Snyder et al., Posttransplant lymphoproliferative disorder following nonmyelopablative allogeneic stem cell transplantation, Am J. Surg Pathol., 28(6):794-800 (2002).

Spyridonidis et al., Minimal residual disease in autologous hematopoietic harvests from breast cancer patients, Ann. Oncol., 9(8):821-826 (1998).

Steele, Recent developments in the virus therapy of cancer, Proc. Soc. Exp. Biol. Med., 223(2):118-127 (2000).

Stewart et al., Superior autologous blood stem cell mobilization from dose-intensive cyclophosphamide, etoposide, cisplatin plus G•CSF than from less intensive chemotherapy regimens, Bone Marrow Transplant, 23(2):111-117 (1999).

Stodjl et al., Exploiting tumor-specific defects in the interferon pathway with a previously unknown oncolytic virus, Nature Medicine, 6(7):821-825 (2000).

Strong et al., The molecular basis of viral oncolysis: usurpation of the ras signaling pathway by reovirus, EMBO J., 17(12):3351-3362 (1998).

Strong et al., The v-erbV oncogene confers enhanced cellular susceptibility to reovirus infection, J. Virol., 70 (1):612-616 (1996).

Strong et al., Evidence that the epidermal growth factor receptor on host cells confers reovirus infection efficiency, Virology, 197(1):405-411 (1993).

Sundaresan et al., Attenuated, replication-competent herpes simplex virus type 1 mutant G207: safety evaluation in mice, J. Virology, 74:3832-3841(2000).

Thimmappaya et al., Adenovirus V AI RNA is required for efficient translation of viral mRNAs at late times after infection, Cell, 31:543-551 (1982).

Toda et al., Treatment of human breast cancer in a brain metastatic model by G207, a replication-competent multimutated herpes simplex virus 1, Hum. Gene Ther., 9(15):2177-2185 (1998).

Ueno et al., Allogeneic peripheral blood progenitor-cell transplantation for poor-risk patients with metastatic breast cancer, J. Clin. Oncol., 16(3):986-993 (1998).

Van Weering et al., Ret receptor tyrosine kinase activates extracellular signal-regulated kinase 2 in SK-N-MC cells, Oncogene, 11:2007-2014 (1995).

Wantanabe et al., Augologous and allogeneic transplantation with peripheral blood CD34+ cells: a pediatric experience, Haematologica, 84:167-176 (1999).

Wiman, New p53-based anti-cancer therapeutic strategies, Med. Oncol.,15(4):222-228 (1998).

Winter, High-dose therapy with stem-cell transplantation in the malignant lymphomas, Onc. (Huntingt), 13 (12):1635-1645 (1999).

Wu et al., Biological purging of breast cancer cells using an attenuated replication-competent herpes simplex virus in human hemotopoietic stem cell transplantation, Cancer Research., 61(7):3009-3015 (2001).

Wu et al., Bone marrow purging of neuroblastoma by attenuated multimutated herpes simplex virus, Proceedings of the American Association for Cancer Research Annual., 39:605, Abstract #4113 (1998).

Wu et al., Proc Annu. Meet AM Soc Clin Oncol., 16:91a, Abstract #319 (1997).

Yazaki et al., Treatment of human malignant meningiomas by G207, a replication-competent multimutated herpes simplex virus 1, Cancer Research, 55:4752-4756 (1995).

Yoon et al., An oncolytic herpes simplex virus type 1 selectively destroys diffuse liver metastases from colon carcinoma, FASEB J., 14(2):301-311 (2000).

Zachos et al., Expression of ras proto-oncogenes: regulation and implications in the development of human tumors, Crit. Rev. Oncology Hematology, 26:65-76 (1997).

Zorn et al., Induction of cytokines and cytotoxicity against tumor cells by Newcastle disease virus, Cancer Biotherapy, 9(3):225-235 (1994).

\* cited by examiner

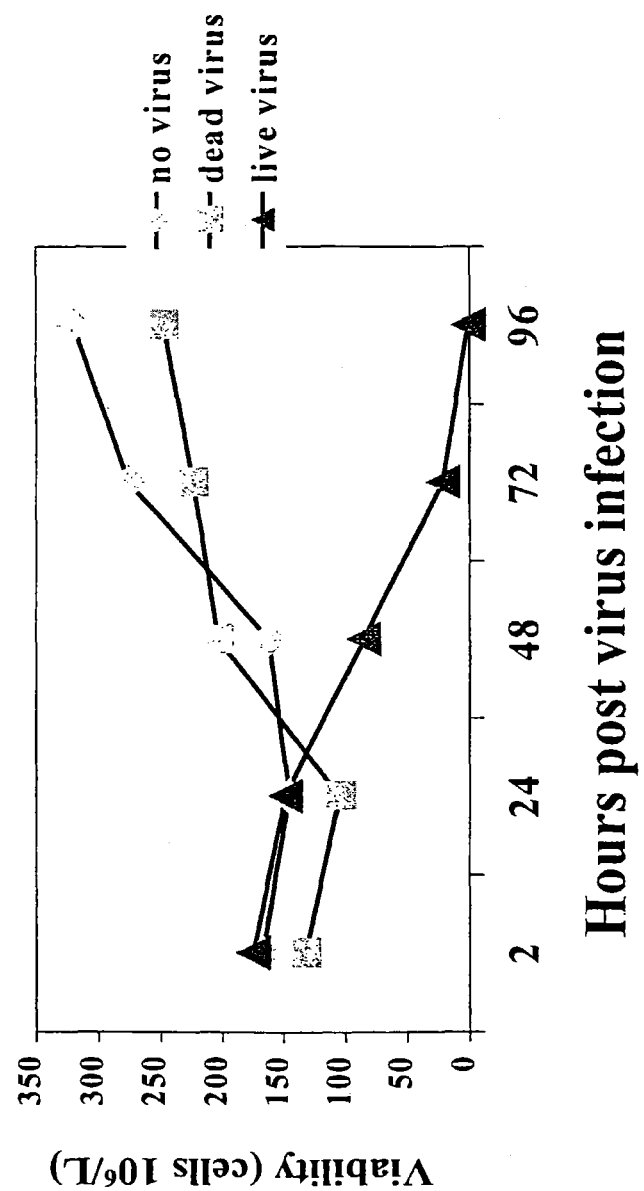
FIGURE 1B Viability - SKBR3

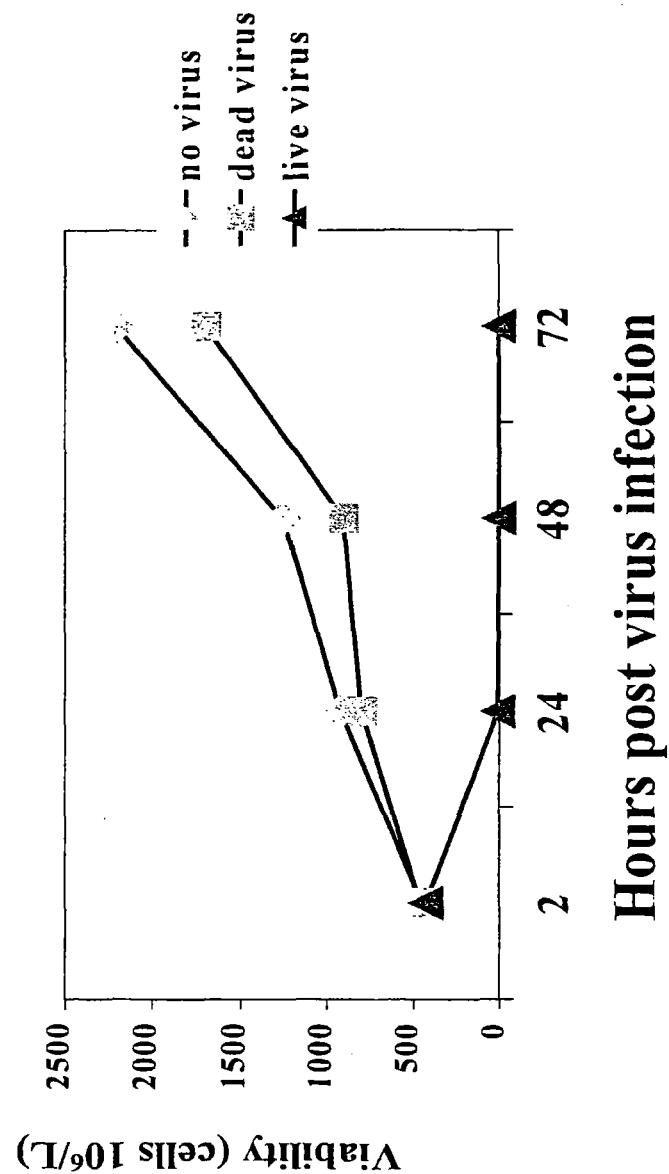

Effect of reovirus on MCF7 viability

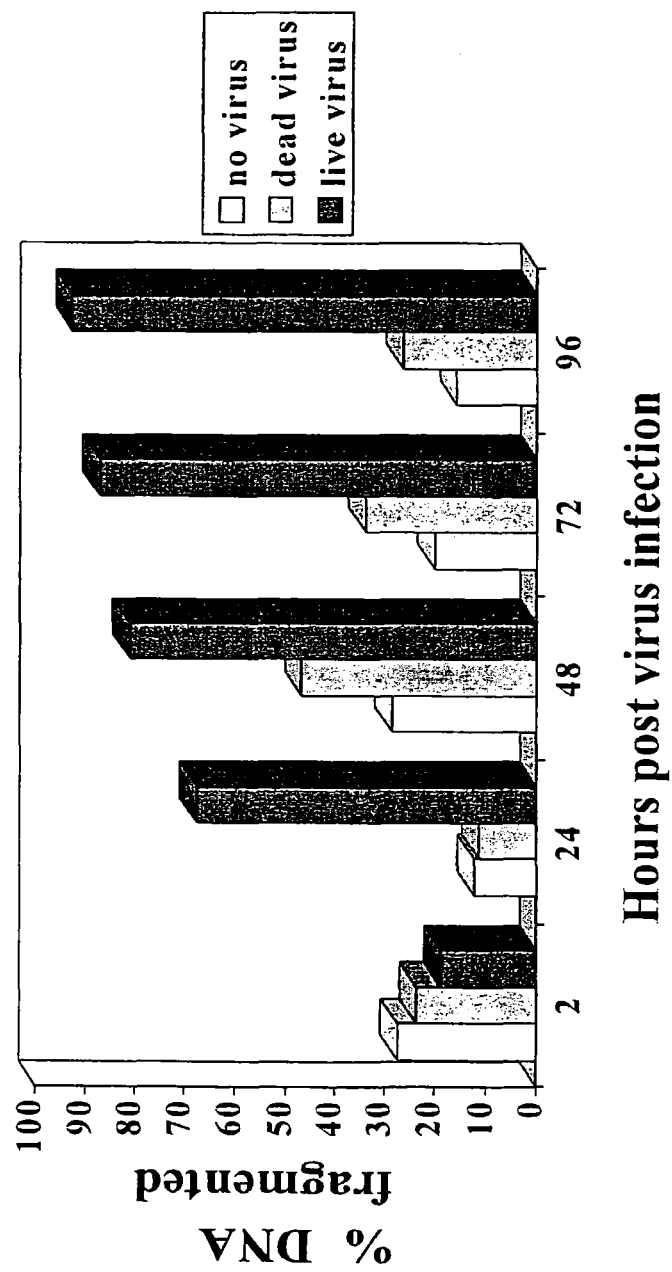

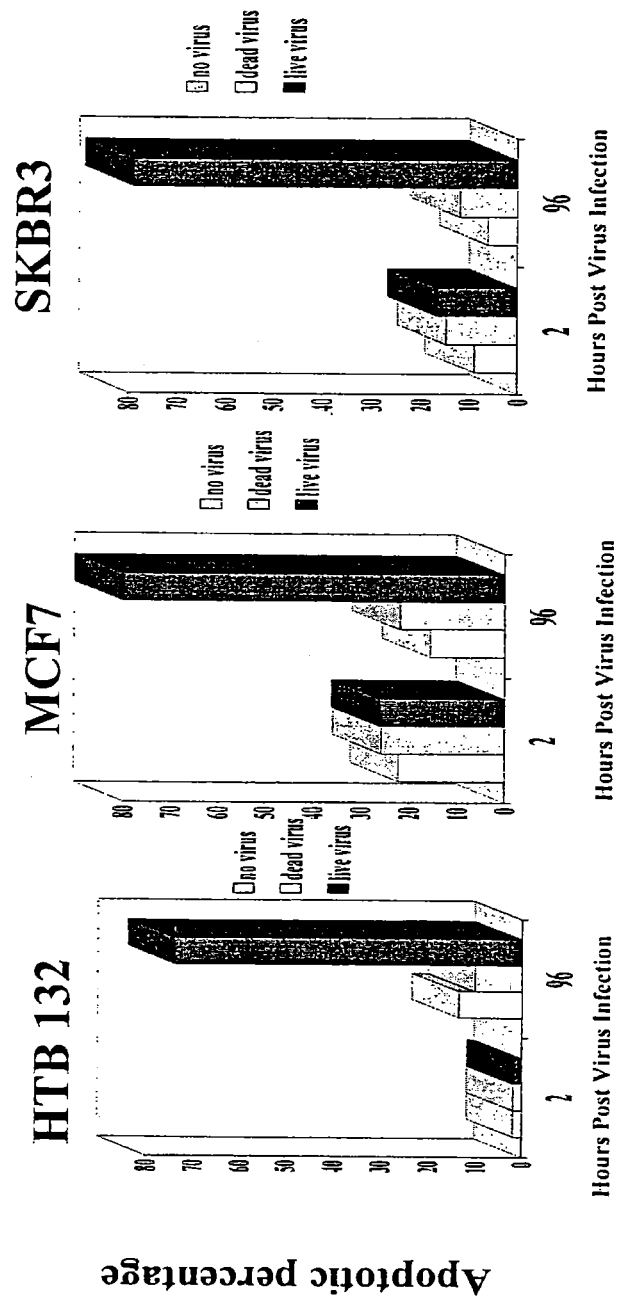

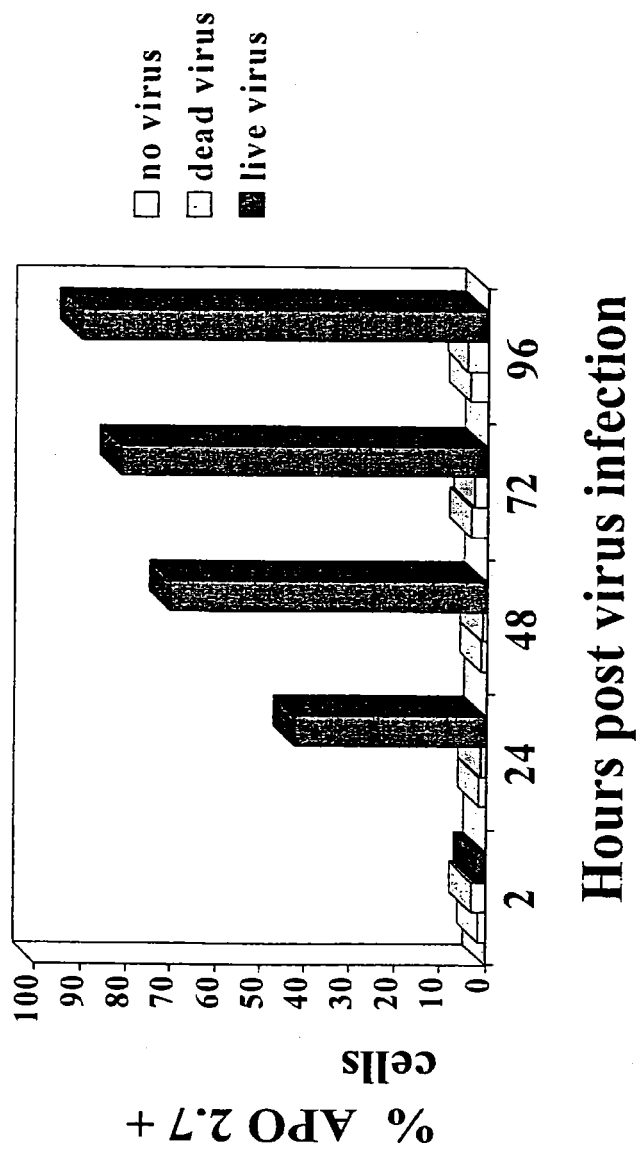

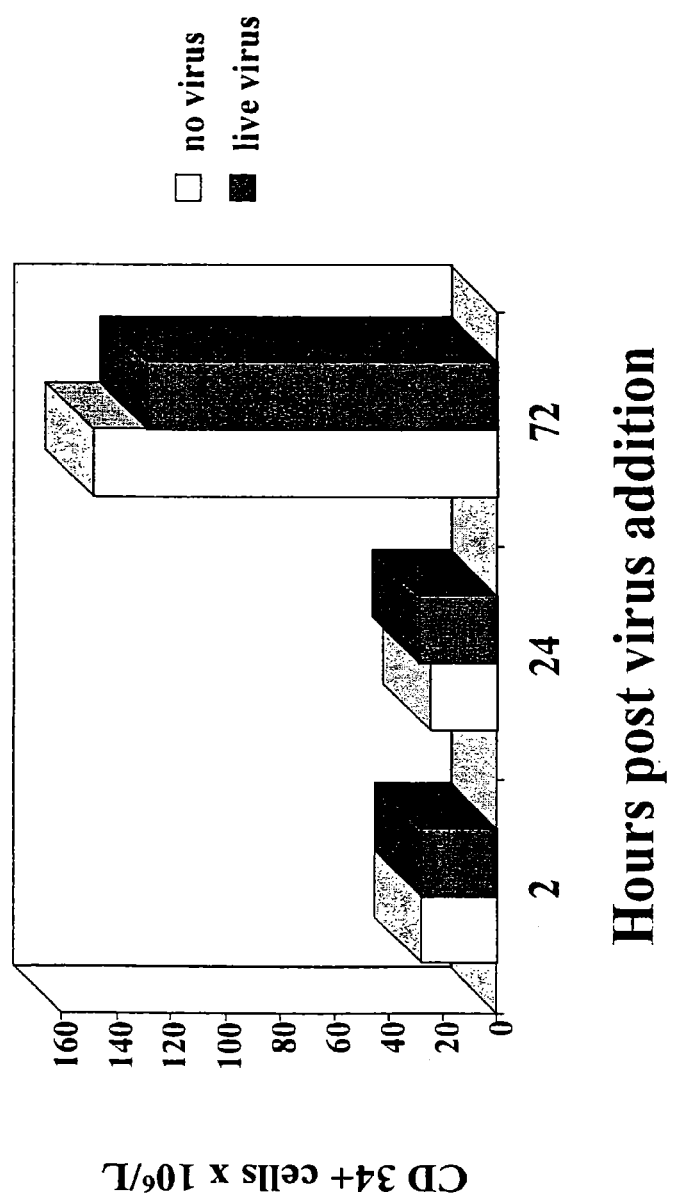

VIRUS CLEARANCE OF NEOPLASTIC CELLS FROM MIXED CELLULAR COMPOSITIONS

RELATED INVENTIONS

The present application is a continuation-in-part of U.S. Ser. No. 12/652,289, filed Jan. 5, 2010, which is a continuation of U.S. Ser. No. 11/807,771, filed May 30, 2007, which is a continuation of U.S. Ser. No. 10/602,024, filed Jun. 24, 2003, now U.S. Pat. No. 7,306,902, which claims the benefit of U.S. Provisional Applications Nos. 60/392,031, filed Jun. 28, 2002, and 60/443,188, filed Jan. 29, 2003. U.S. application Ser. No. 12/652,289 is also a continuation-in-part of U.S. Ser. No. 10/931,728, filed Aug. 31, 2004, which is a divisional of U.S. Ser. No. 09/847,355, filed May 3, 2001, which claims priority to U.S. Provisional Application Ser. No. 60/276,782, filed Mar. 16, 2001; Ser. No. 60/268,054, filed Feb. 13, 2001; Ser. No. 60/205,389, filed May 19, 2000; and Ser. No. 60/201,990, filed May 3, 2000. The present application is also a continuation of U.S. Ser. No. 11/807,921, filed May 30, 2007, which is a continuation of U.S. Ser. No. 10/931,728, filed Aug. 31, 2004, which is a divisional of U.S. Ser. No. 09/847,355, filed May 3, 2001, which claims priority to U.S. Provisional Applications Nos. 60/276,782, filed Mar. 16, 2001; 60/268,054, filed Feb. 13, 2001; 60/205,389, filed May 19, 2000; and 60/201,990, filed May 3, 2000. The entire disclosure of each of the above-mentioned applications is hereby incorporated by reference.

FIELD OF THE INVENTION

The present invention relates to a method of selectively removing neoplastic cells from a mixed cellular composition outside of a living organism by using a virus which selectively infects and kills the neoplastic cells. Also provided are compositions prepared according to this method, and kits comprising a combination of viruses which are useful in this invention.

REFERENCES

U.S. Pat. No. 6,136,307.
WO 94/18992, published Sep. 1, 1994.
WO 94/25627, published Nov. 10, 1994.
WO 99/08692, published Feb. 25, 1999.
Bar-Eli, N., et al., "preferential cytotoxic effect of Newcastle disease virus on lymphoma cells", *J. Cancer Res. Clin. Oncol.* 122: 409-415 (1996).
Bensinger, W. I., "Should we purge?", *Bone Marrow Transplant.* 21:113-115 (1998).
Bischoff J R. et al., "An Adenovirus Mutant that Replicates Selectively in p53-Deficient Human Tumor", *Science* 274 (5286):373-6 (1996).
Blagoslelonny, M. V., et al., "in vitro Evaluation of a p53-Expressing Adenovirus as an Anti-Cancer Drug", *Int. J. Cancer* 67(3):386-392 (1996).
Bos, J. L., "Ras Oncogenes in Human Cancer: A Review", *Canc. Res.* 49(17): 4682-4689 (1989).
Brooks et al., eds. "Jawetz, Melnick & Adelberg's Med. Microbiology". (1998).
Chang et al., *PNAS* 89:4825-4829 (1992).
Chang, H. W. et al., *Virology* 194:537-547 (1993).
Chang et al., *J. Virol.* 69:6605-6608 (1995).
Coffey, M. C., et al., "Reovirus Therapy of Tumors with Activated Ras Pathway", *Science* 282:1332-1334 (1998).
Duggan, P. R., et al., "Predictive factors for long-term engraftment of autologous blood stem cells", *Bone Marrow Transplantation* 26(12): 1299-1304 (2000).
Fueyo, J., et al., "A Mutant Oncolytic Adenovirus Targeting the Rb Pathway Produces Anti-Glioma Effect in Vivo", *Oncogene* 19(1):2-12 (2000).
Gao, J., B. Tombal and J. T. Isaacs, "Rapid in situ hybridization technique for detecting malignant mouse cell contamination in human xenograft tissue from nude mice and in vitro cultures from such xenografts", *Prostate* 39(1): 67-70 (1999).
Haig, D. M., et al., *Immunology* 17:4146-4158 (1997).
He, B., et al., *Proc. Nat. Acad. Sci.* 94: 843-848 (1997).
Kawagishi-Kobayashi, M., et al., *Mol. Cell. Biology* 17:4146-4158 (1997).
Nemunaitis, J., *Invest. New Drugs* 17:375-386 (1999).
Nielsen L L., et al., "P53 Tumor Suppressor Gene Therapy for Cancer", *Cancer Gene Ther.* 5(1):52-63 (1998).
Nieto, Y. et al., "Autologous stem-cell transplantation for solid tumors in adults", *Hematol. Onthl. Clin. North Am.* 13(5):939-968 (1999).
Norman, K., et al., "Reovirus as a novel oncolytic agent", *J. Clin. Invest.* 105 (8): 1035-1038 (2000).
Reichard, K. W., et al., "Newcastle Disease Virus Selectively Kills Human Tumor Cells", *J. of Surgical Research* 52:448-453 (1992).
Stojdl, D. F., et al., "Exploiting Tumor-Specific Defects in the Interferon Pathway with a Previously Unknown Oncolytic Virus", *Nat. Med.* 6(7):821-825 (2000).
Romano et al., *Mol. and Cell. Bio.* 18:7304-7316 (1998).
Sharp et al., *Virol.* 250:301-315 (1998).
Spyridonidis, A. et al., "Minimal residual disease in autologous hematopoietic harvests from breast cancer patients", *Annals of Onc.* 9:821-826 (1998).
Steele, T. A., "Recent Developments in the Virus Therapy of Cancer", *Proc. Soc. Exp. Biol. Med.* 223:118-127 (2000).
Stewart, D. A., et al., "Superior autologous blood stem cell mobilization from dose-intensive cyclophosphamide, etoposide, cisplatin plus G-CSF than from less intensive chemotherapy regimens", *Bone Marrow Transplant.* 23(2): 111-117 (1999).
Strong, J. E., et al., "The Molecular Basis of Viral Oncolysis: Usurpation of the Ras Signaling Pathway by Reovirus", *EMBO J.* 17:3351-3362 (1998).
Strong, J. E., et al., "Minimal Residual Disease in Autologous Hematopietic Harvests from Breast Cancer Patients", *Annals of Onc.* 9:821-826 (1998).
Strong, J. E., et al., "Evidence that the Epidermal Growth Factor Receptor on Host Cells Confers Reovirus Infection Efficiency", *Virology* 197(1):405-411 (1993).
Strong, J. E., et al., "The v-erbV oncogene confers enhanced cellular susceptibility to reovirus infection", *J. Virol.* 70:612-616 (1996).
Wiman K G, "New p53-Based Anti-Cancer Therapeutic Strategies", *Med Oncol.* 15(4):222-8 (1998).
Winter, J. N., "High-dose therapy with stem-cell transplantation in the malignant lymphomas", *Onc. (Huntingt)* 13(12):1635-1645 (1999).
Yoon, S. S., et al., "An Oncolytic Herpes Simplex Virus Type I Selectively Destroys Diffuse Liver Metastases from Colon Carcinoma", *FASEB J.* 14:301-311 (2000).
Zorn, U. et al., "Induction of Cytokines and Cytotoxicity against Tumor Cells by Newcastle Disease Virus", *Cancer Biotherapy* 9(3):22-235 (1994).

All of the above publications, patents and patent applications are herein incorporated by reference in their entirety to the same extent as if the disclosure of each individual publication, patent application or patent was specifically and individually indicated to be incorporated by reference in its entirety.

BACKGROUND OF THE INVENTION

Cell proliferation is regulated by both growth-promoting signals and growth-constraining signals. These two kinds of signals for each cell would normally strike a balance in a manner which reflects the need of the body for the particular cell. If a cell fails to respond to the growth-constraining signals or over-responds to the growth-promoting signals, it will proliferate abnormally fast (referred to as neoplastic cells) and may eventually develop into cancer, a malignant neoplasm.

Chemotherapy, a current method of treating cancer, is generally based on the fast-proliferating property of cancer cells. Since cancer cells proliferate rapidly, they are more sensitive to drugs which inhibit cellular proliferation. In theory, by carefully choosing the dosage of chemotherapeutic drugs, one can inhibit cancer cell proliferation without seriously damaging normal cells. However, some normal cells, such as hematopoietic stem cells, also proliferate rapidly. Therefore, any dosage which is harmful to cancer cells is often also harmful to the hematopoietic stem cells. On the other hand, if the dosage is not high enough to kill the cancer cells, there is a risk that the cancer would reappear shortly after chemotherapy is terminated.

Because it is hard to find a dosage which selectively kills cancer cells, high-dose chemotherapy followed by autologous hematopoietic progenitor stem cell transplantation has gained extensive application as a therapeutic approach in many cancers (for example, see Winter, 1999; Nieto and Shpall, 1999). In this approach, a portion of the hematopoietic stem cells is removed from a cancer patient, and the patient is then treated with high-dose chemotherapy which is lethal to rapid-proliferating cells, such as cancer cells and hematopoietic stem cells. Subsequently, the patient receives transplantation of autologous hematopoietic stem cells, which have been previously removed from the same patient, to regenerate the hematopoietic system.

A serious drawback of this therapy is that when the hematopoietic progenitor stem cells are removed from the patients, they are often contaminated with cancer cells. This is especially a problem when the patient has a cancer of hematopoietic origin, but patients with a solid tumor may also suffer from contamination of the hematopoietic stem cells, particularly if the solid tumor has metastasized. As a result, when the removed cells are transplanted back to reestablish the hematopoietic system, some cancer cells may also be placed back to the cancer patient where they may proliferate again to contribute to cancer recurrence. It is therefore desirable to purge the autografts before transplantation.

Several methods have been employed to purge autografts (Spyridonidis et al, 1998; Bensinger 1998). The autograft can be treated with chemotherapy to kill the contaminating neoplastic cells in vitro. However, as discussed above, it is hard to find a dosage for the chemotherapeutic drug which selectively kills neoplastic cells or cancer cells but leaves normal hematopoietic stem cells intact. Autografts can also be treated with a toxin conjugated to antibodies which recognize an antigen that is specific for the neoplastic cells, but such a tumor specific antigen does not always exist. It is also possible to separate stem cells from the other cells based on a stem cell specific surface marker (CD34) by using flow cytometry, affinity columns or magnetic beads. However, by selecting only certain hematopoietic cells, e.g., the $CD34^+$ cells, other hematopoietic cells such as T cells, B cells, monocytes and natural killer cells are also eliminated, and immune recovery may be delayed (Bensinger, 1998). This method also results in the loss of about half the $CD34^+$ cells and retention of some contaminating cancer cells (Spyridonidis et al., 1998).

Therefore, there remains a need for a highly selective method with a reasonable yield to purge autografts which may contain neoplastic cells.

SUMMARY OF THE INVENTION

The present invention is directed to a method of selectively removing neoplastic cells from a mixed cellular composition, for example an autograft, by using a virus which exhibits selective killing of neoplastic cells. A variety of viruses are capable of selectively removing neoplastic cells but not normal cells. For example, reovirus selectively kills ras-activated neoplastic cells, viruses expressing a wild type p53 gene are selective for neoplastic cells with a dysfunctional p53, and any interferon sensitive virus is selective for neoplastic cells having a disrupted interferon pathway.

Accordingly, one aspect of the present invention is directed to a method of selectively removing neoplastic cells from a mixed cellular composition suspected of containing neoplastic cells wherein said composition is located outside of a living organism, said method comprising the steps of: (a) contacting the mixed cellular composition with a virus under conditions which result in substantial killing of the neoplastic cells; and (b) collecting the treated cellular composition.

In another embodiment of the invention, the method further comprises the step of freezing and storing the virus-treated cellular composition in a solution containing DMSO. DMSO is routinely used to freeze and store animal cells but it can denature viruses. Therefore, DMSO treatment removes infectious virus from the cellular composition while preserving the activity of the composition in the frozen state for a prolonged period of time.

In another embodiment of the present invention, the virus is removed from the virus-treated cellular composition by subjecting the mixture to anti-virus antibodies which are specific for the particular virus, or a combination of anti-virus antibodies and complement in order to lyse the virus. Alternatively or additionally, anti-virus antibodies which recognize a molecule on the surface of the virus particle may be used to remove the virus particles by immobilizing the antibodies, applying the cellular composition to the immobilized antibodies, and collecting the part of the composition which does not bind to the antibodies.

Similarly, specific antibodies against the particular virus can be administered to the transplant recipient to eliminate the virus in vivo, or the recipient can be given an immune system stimulant to achieve this purpose.

In another embodiment of the present invention, the virus is removed from the virus-treated cellular composition by using a gradient which can separate viruses from cells.

In a preferred embodiment of this invention, the mixed cellular composition comprises hematopoietic stem cells. Thus, hematopoietic stem cells can be purged prior to transplantation, or any other desired use, to remove the neoplastic cells. The hematopoietic stem cells can be harvested from bone marrow or blood.

The application of this invention is not limited to purging hematopoietic stem cells. In another embodiment of this invention, the present method can be applied to any tissue, organ, a combination of different tissues/organs, or any portion of a tissue or an organ to remove neoplastic cells. The tissues or organs are preferably useful in a subsequent transplantation. However, the present method is also useful in purging tissues or organs for any other purposes wherein it is desirable to remove neoplastic cells which are present in the tissue or organ.

In another embodiment of the invention, a virus is used to treat cultured cell lines to remove cells which are spontaneously transformed. This method can also be used to treat semen or donor eggs before artificial insemination or other reproduction-related procedures.

In another aspect of this invention, the virus is a replication competent virus. As opposed to a replication-deficient virus, a replication competent virus can replicate in a cell which is susceptible to this virus and often causes this cell to lyse. The replication competent virus useful in this invention can selectively lyse neoplastic cells in a phenomenon termed "oncolysis", but it does not lyse normal cells.

In another embodiment of this invention, the virus is a mutated or modified virus selected from the group consisting of adenovirus, herpes simplex virus, vaccinia virus and parapoxvirus orf. Each of these viruses in the native form has developed a mechanism to inhibit the double stranded RNA protein kinase (PKR) to facilitate viral protein synthesis which is otherwise inhibited by PKR. These viruses can therefore replicate in any cells regardless of PKR. When these viral PKR inhibitors are mutated or modified, however, the virus is then susceptible to PKR inhibition and does not replicate in normal cells, which have a functional PKR pathway. These mutated or modified viruses can be used to selectively remove ras-activated neoplastic cells because ras-activated neoplastic cells are deficient in PKR function and thus can not inhibit replication of these viruses.

In another aspect of this invention, the virus selectively kills neoplastic cells by carrying a tumor suppressor gene. For example, p53 is a cellular tumor suppressor which inhibits uncontrolled proliferation of normal cells. Approximate half of all tumors have functionally impaired p53 and proliferate in an uncontrolled manner. Therefore, a virus which expresses the wild type p53 gene can selectively kill the neoplastic cells which become neoplastic due to inactivation of the p53 gene product.

A similar embodiment involves viral inhibitors of cellular tumor suppressor genes. Certain viruses encode a protein which inhibits tumor suppressors, thereby allowing viral replication in the cell. By mutating these viral inhibitors, a virus is generated which does not replicate in normal cells due to the presence of tumor suppressors. However, it replicates in neoplastic cells which have lost the tumor suppressors and can be used to selectively kill neoplastic cells in the present invention.

In another embodiment of the invention, an interferon-sensitive virus is used to selectively kill neoplastic cells. An interferon-sensitive virus is inhibited by interferon and does not replicate in a normal cell which has an intact interferon pathway. Since some neoplastic cells have their interferon pathway disrupted, they can be selectively killed by an interferon sensitive virus. The interferon sensitive virus is preferably vesicular stomatitis virus (VSV). Interferon can be optionally added along with the interferon sensitive virus to remove neoplastic cells.

Also provided are cellular compositions which have been treated with a virus to remove neoplastic cells and leave viable non-neoplastic cells. Such compositions may be used for in vitro research, or in transplantation, insemination, or other in vivo procedures. The transplantation may be autologous, allogeneic, or even xenogeneic. Preferably the transplantation is autologous. More preferably, the composition comprises hematopoietic stem cells.

Another aspect of the invention provides a kit which comprises at least two viruses with different selectivity, such as reovirus, a virus expressing a functional p53 protein, Delta24, ONYX-015, Newcastle disease virus or vesicular stomatitis virus.

BRIEF DESCRIPTION OF THE DRAWINGS

FIGS. 1A-1C show the number of viable cells in MCF7 (FIG. 1A), SKBR3 (FIG. 1B) or HTB 132 (FIG. 1C) which were infected with live reovirus, dead virus or no virus as indicated.

FIG. 2 shows that apoptosis was induced by reovirus infection in MCF7, SKBR3 or HTB 132 cells. FIGS. 2A-2C demonstrate the percentage DNA which were fragmented after reovirus infection. FIG. 2D shows the percentage of the apoptotic marker Annexin V staining after reovirus infection. FIGS. 2E-2G show the percentage of APO2.7$^+$ cells in each cell type as indicated.

FIG. 3A shows the number of viable cells at various time points after CD34$^+$ stem cells had been infected with reovirus.

DETAILED DESCRIPTION OF THE INVENTION

Figure 1A:
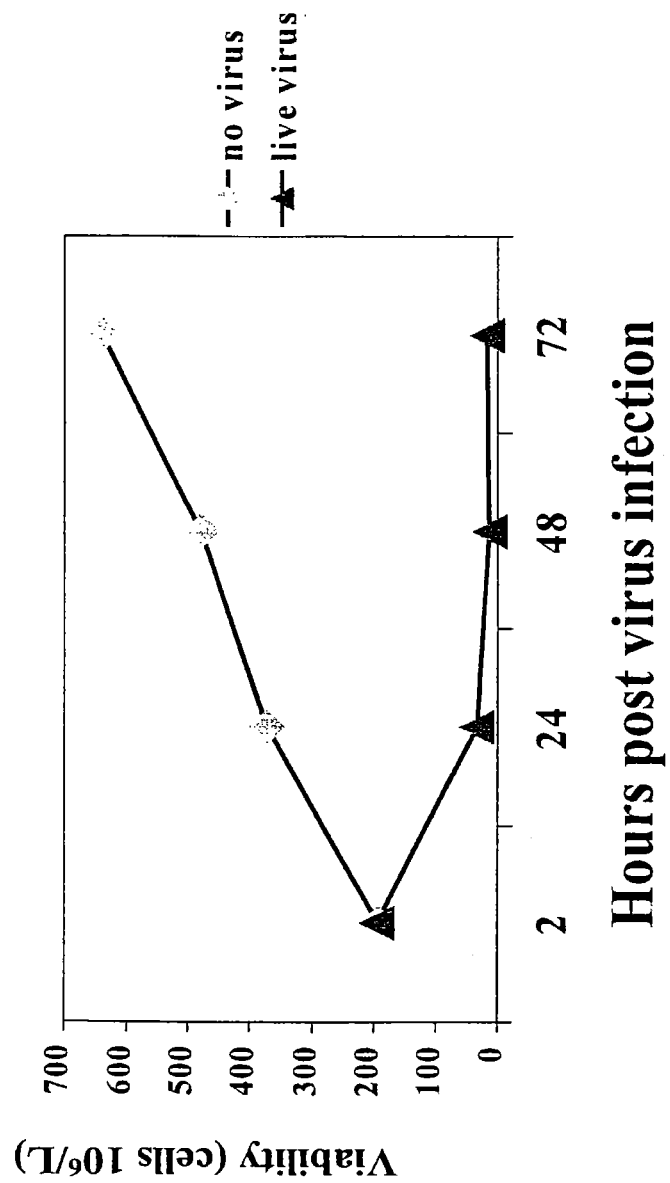
Figure 1D:
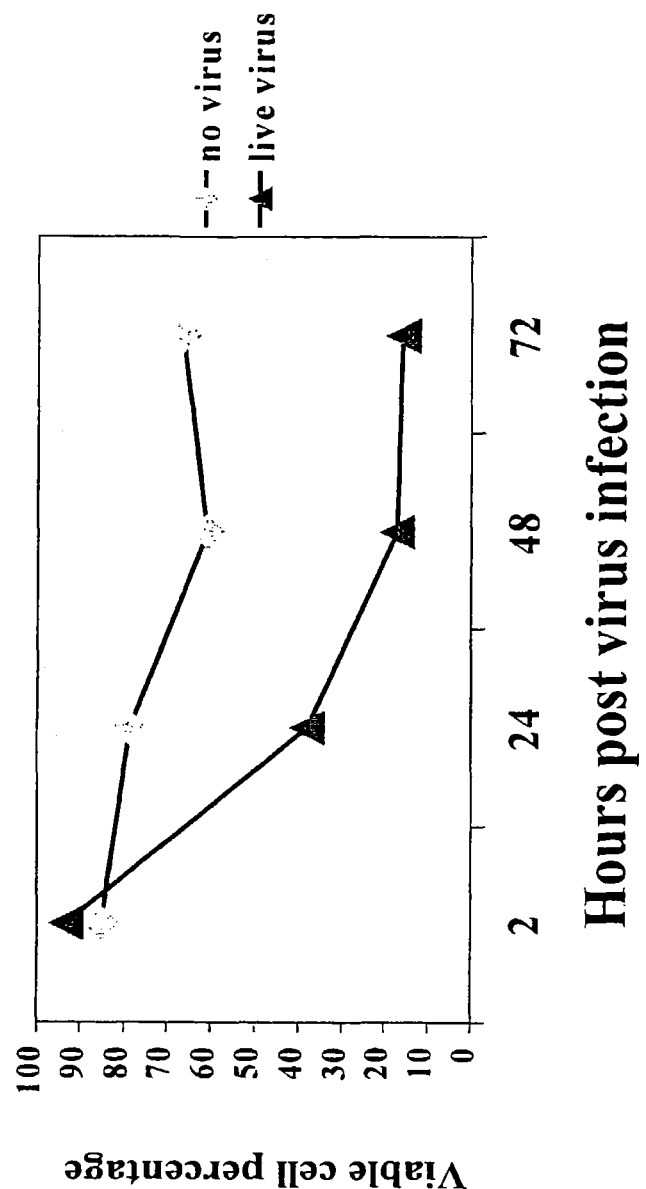
FIG. 1D shows the percentage of MCF7 cells which were viable at various time points after reovirus infection.
Figure 2A:
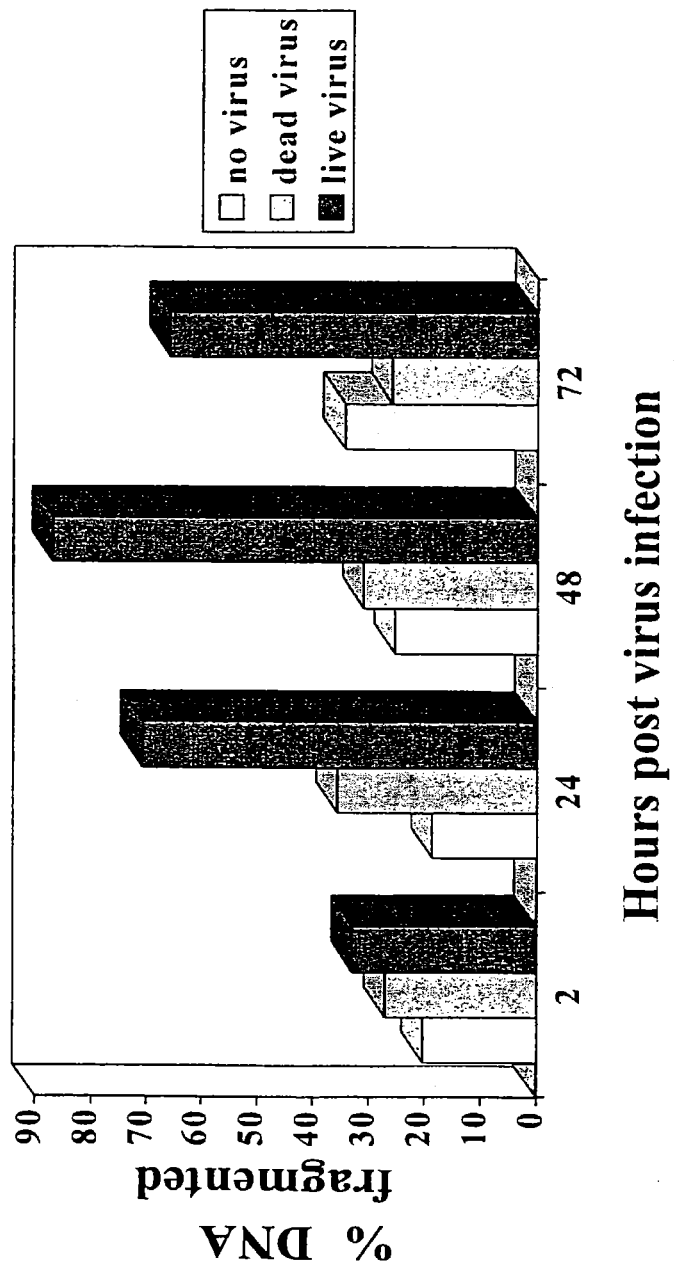
Figure 2B:
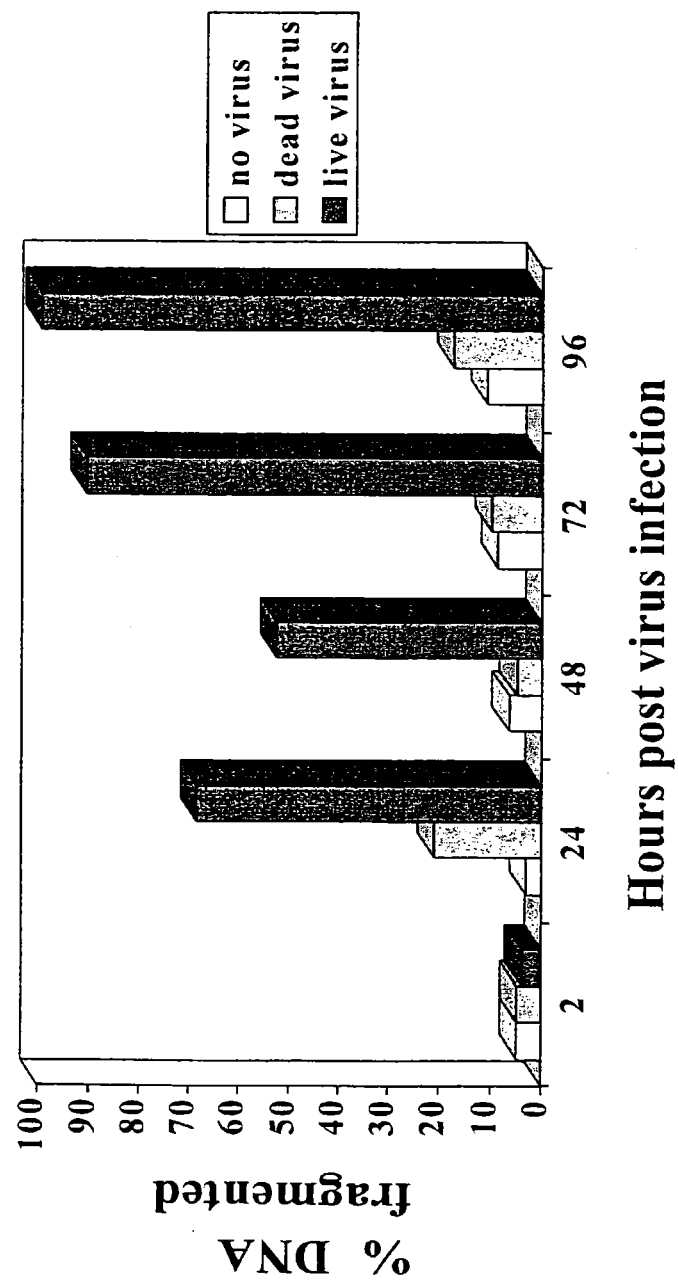
Figure 2E:
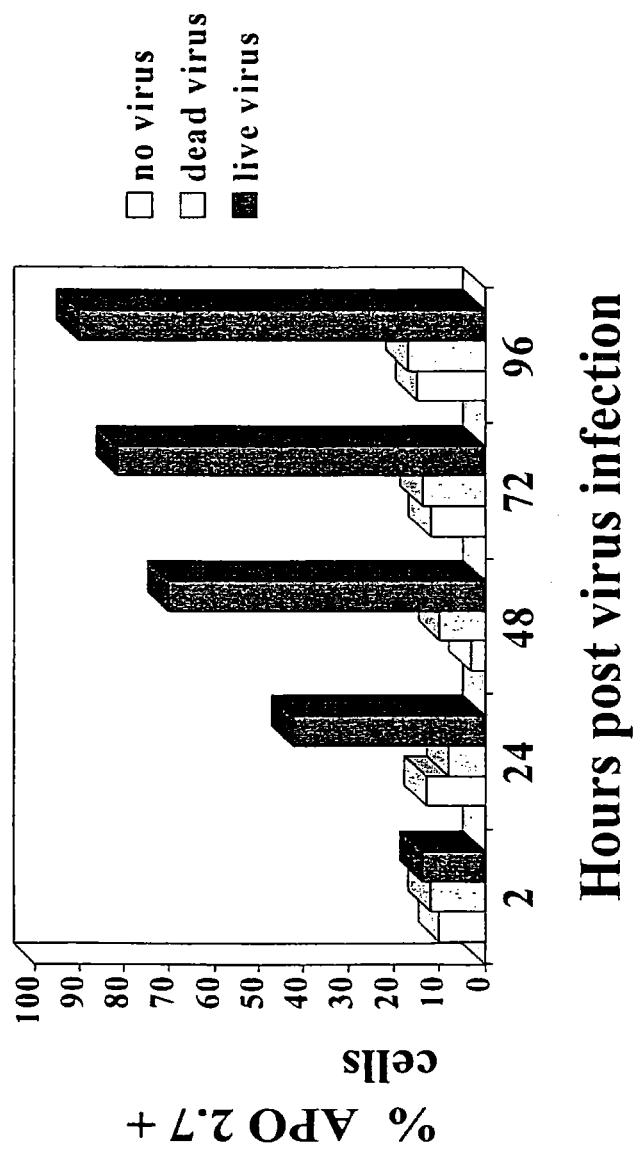
Figure 2G:
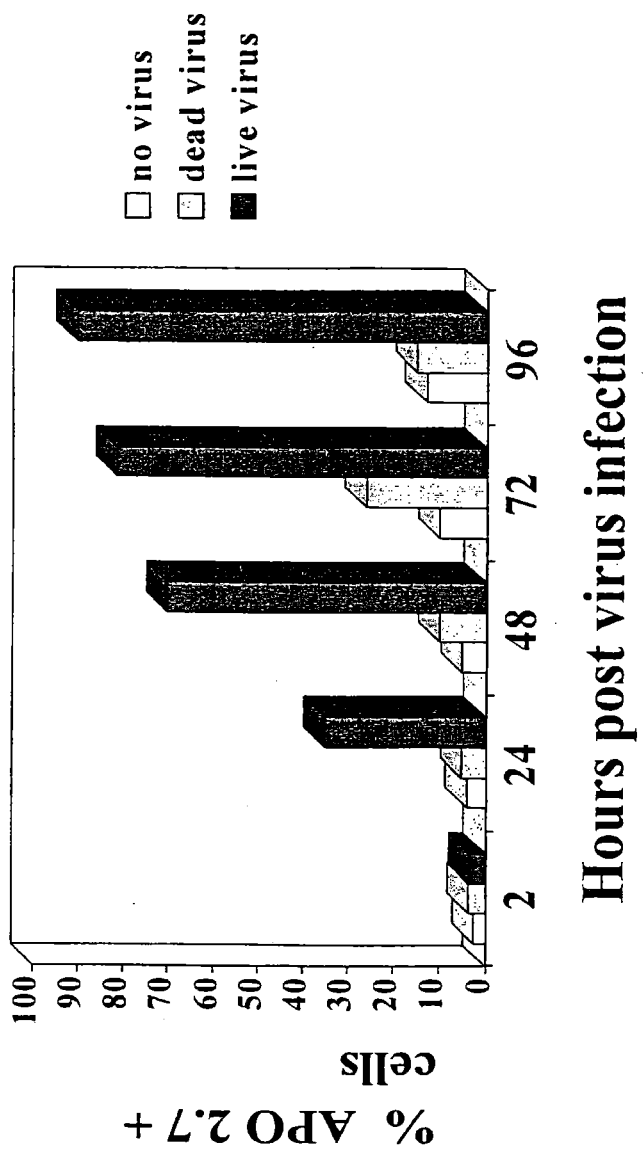

The present invention is directed to a method for selectively removing neoplastic cells from a mixed cellular composition, for example an autograft, by using a virus which exhibits selective killing of neoplastic cells. A variety of viruses are useful in this invention. For instance, a mixed cellular composition can be treated with reovirus, which selectively kills ras-activated neoplastic cells. Ras-activated neoplastic cells may also be selectively removed with a virus in which the viral inhibitor of double stranded protein kinase (PKR) is mutated or modified. If the composition is suspected of containing p53-deficient tumor cells, it can be treated with a virus expressing the p53 tumor suppressor gene, which induces apoptosis in tumor cells with functional impairment in the p53 gene product (Wiman, 1998; Nielsen et al., 1998). Vesicular stomatitis virus (VSV) or other interferon sensitive viruses can be used in the presence of interferon to kill neoplastic cells with a disrupted interferon pathway.

Other examples of viruses useful in this invention include vaccinia virus, influenza virus, varicella virus, measles virus, herpes virus and Newcastle Disease Virus, which were reported to be associated with tumor regression or death (Nemunaitis, 1999). However, this invention encompasses any virus which is capable of selectively killing neoplastic cells.

Prior to describing the invention in further detail, the terms used in this description are defined as follows unless otherwise indicated.

DEFINITIONS

"Virus" refers to any virus, whether in the native form, attenuated or modified. Modified viruses include chemically modified viruses or recombinantly modified viruses. A recombinantly modified virus may be a mutated virus, a recombinant virus or a reassorted virus. A mutated virus is a virus in which the viral genome has been mutated, namely having nucleotide insertions, deletions and/or substitutions. A recombinant virus is a virus having coat proteins from different subtypes, usually prepared by co-infecting a cell with more than one subtype of the virus, resulting in viruses which are enveloped by coat proteins encoded by different subtypes. A reassorted virus is a multi-segment virus in which the segments have been reassorted, usually by co-infecting a cell with more than one subtype of this virus so that the segments from different subtypes mix and match in the cell.

"Neoplastic cells", also known as "cells with a proliferative disorder", refer to cells which proliferate without the normal growth inhibition properties. A new growth comprising neoplastic cells is a neoplasm or tumor. A neoplasm is an abnormal tissue growth, generally forming a distinct mass, which grows by cellular proliferation more rapidly than normal tissue growth. Neoplasms may show partial or total lack of structural organization and functional coordination with normal tissue. As used herein, a neoplasm is intended to encompass hematopoietic neoplasms as well as solid neoplasms.

A neoplasm may be benign (benign tumor) or malignant (malignant tumor or cancer). Malignant tumors can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoietic structures (structures pertaining to the formation of blood cells) including components of the immune system, are called leukemias and lymphomas. Other neoplasms include, but are not limited to neurofibromatosis.

"Ras-activated neoplastic cells" or "ras-mediated neoplastic cells" refer to cells which proliferate at an abnormally high rate due to, at least in part, activation of the ras pathway. The ras pathway may be activated by way of ras gene structural mutation, elevated level of ras gene expression, elevated stability of the ras gene message, or any mutation or other mechanism which leads to the activation of ras or a factor or factors downstream or upstream from ras in the ras pathway, thereby increasing the ras pathway activity. For example, activation of EGF receptor, PDGF receptor or Sos results in activation of the ras pathway. Ras-mediated neoplastic cells include, but are not limited to, ras-mediated cancer cells, which are cells proliferating in a malignant manner due to activation of the ras pathway.

"Cellular composition" means a composition comprising cells. The composition may contain non-cellular matter. For example, whole blood is a cellular composition which contains plasma, platelets, hormones and other non-cellular matter in addition to cells such as erythrocytes and leukocytes. A cellular composition may contain cells of various types, origin or organization. For example, tissues and organs which contain different cell types arranged in defined structures are considered cellular compositions.

A "mixed cellular composition" is a cellular composition containing at least two kinds of cells. Typically, the mixed cellular composition contains both normal cells and neoplastic cells. It is preferable that most of the cells in the cellular composition are dividing cells, and the virus selectively kills neoplastic cells but leaves other dividing cells essentially intact.

A cellular composition "suspected of containing neoplastic cells" is a cellular composition which may contain neoplastic cells. For example, any autograft obtained from a subject bearing a neoplasm may contain neoplastic cells. A cell culture which has been in culture for a considerable amount of time may contain spontaneous by neoplastic cells.

"Substantial killing" means a decrease of at least about 20% in viability of the target neoplastic cells. The viability can be determined by a viable cell count of the treated cells, and the extent of decrease can be determined by comparing the number of viable cells in the treated cells to that in the untreated cells, or by comparing the viable cell count before and after virus treatment. The decrease in viability is preferably at least about 50%, more preferably at least about 70%, still more preferably at least about 80%, and most preferably at least about 90%.

The neoplastic cells may be killed in various manners. For example, they may be lysed by a virus which is capable of lytic infection of neoplastic cells (oncolysis). The neoplastic cells may undergo apoptosis which is induced directly or indirectly by the virus. The cells may also, although less preferably, be killed by the immune system which has been activated by the virus. For example, the virus may induce cytokine production, which activates the natural killer cells, which in turn selectively kills neoplastic cells (Zorn et al., 1994).

A "replication competent" virus is a virus which is capable of replicating in at least one cell type. As opposed to a replication competent virus, a "replication incompetent virus" contains a mutation in a region of its genome which is essential for its replication, and hence is not capable of replicating in any cell.

"Adenovirus" is a double stranded DNA virus of about 3.6 kilobases. In humans, adenoviruses can replicate and cause disease in the eye and in the respiratory, gastrointestinal and urinary tracts. About one-third of the 47 known human serotypes are responsible for most cases of human adenovirus disease (Brooks et al., 1998).

The term "mutated adenovirus" or "modified adenovirus" means, as used herein, that the gene product or products which prevent the activation of PKR are lacking, inhibited or mutated such that PKR activation is not blocked. The adenovirus encodes several gene products that counter antiviral host defense mechanisms. The virus-associated RNA (VAI RNA or VA RNA$_i$) of the adenovirus are small, structured RNAs that accumulate in high concentrations in the cytoplasm at late time after adenovirus infection. These VAI RNA bind to the double stranded RNA (dsRNA) binding motifs of PKR and block the dsRNA-dependent activation of PKR by autophosphorylation. Thus, PKR is not able to function and the virus can replicate within the cell. The overproduction of virons eventually leads to cell death. In a mutated or modified adenovirus, the VAI RNA's are preferably not transcribed. Such mutated or modified adenovirus would not be able to replicate in normal cells that do not have an activated Ras-pathway; however, it would be able to infect and replicate in cells having an activated Ras-pathway.

"Herpes simplex virus" (HSV) refers to herpes simplex virus-1 (HSV-1) or herpes simplex virus-2 (HSV-2). HSV gene $_{\gamma 1}$34.5 encodes the gene product infected-cell protein 34.5 (ICP34.5) that can prevent the antiviral effects exerted by PKR. ICP34.5 has a unique mechanism of preventing PKR activity by interacting with protein phosphatase 1 and redirecting its activity to dephosphorylate eIF-2α (He et al., 1997). In cells infected with either wild-type or the genetically engineered virus from which the $_{\gamma1}$34.5 genes were deleted, eIF-2α is phosphorylated and protein synthesis is turned off in cells infected with $_{\gamma1}$34.5 minus virus. It would be expected that the $_{\gamma1}$34.5 minus virus would be replication competent in cells with an activated Ras pathway in which the activity of ICP34.5 would be redundant.

The term "mutated HSV" or "modified HSV" means, as used herein, that the gene product or products which prevent the activation of PKR are lacking, inhibited or mutated such that PKR activation is not blocked. Preferably, the HSV gene $_{\gamma1}$34.5 is not transcribed. Such mutated or modified HSV would not be able to replicate in normal cells that do not have an activated Ras-pathway, however, it would be able to infect and replicate in cells having an activated Ras-pathway.

"Parapoxvirus orf" is a poxvirus. It is a virus that induces acute cutaneous lesions in different mammalian species, including humans. Parapoxvirus orf naturally infects sheep, goats and humans through broken or damaged skin, replicates in regenerating epidermal cells and induces pustular lesions that turn to scabs (Haig et al., 1998). The parapoxvirus orf encodes the gene OV20.0L that is involved in blocking PKR activity (Haig et al., 1998).

The term "mutated parapoxvirus orf" or "modified parapoxvirus orf" means, as used herein, that the gene product or products which prevent the activation of PKR are lacking, inhibited or mutated such that PKR activation is not blocked. Preferably, the gene OV20.0L is not transcribed. Such mutated or modified parapoxvirus orf would not be able to replicate in normal cells that do not have an activated Ras-pathway, however, it would be able to infect and replicate in cells having an activated Ras-pathway.

"Vaccinia virus" refers to the virus of the orthopoxvirus genus that infects humans and produces localized lesions (Brooks et al., 1998). Vaccinia virus encodes two genes that play a role in the down regulation of PKR activity through two entirely different mechanisms. E3L gene encodes two proteins of 20 and 25 kDa that are expressed early in infection and have dsRNA binding activity that can inhibit PKR activity. Deletion or disruption of the E3L gene creates permissive viral replication in cells having an activated Ras pathway. The K3L gene of vaccinia virus encodes pK3, a pseudosubstrate of PKR.

The term "mutated vaccinia virus" or "modified vaccinia virus" means, as used herein, that the gene product or products which prevent the activation of PKR are lacking, inhibited or mutated such that PKR activation is not blocked. Preferably, the E3L gene and/or the K3L gene is not transcribed. Such mutated or modified vaccinia virus would not be able to replicate in normal cells that do not have an activated Ras-pathway, however, it would be able to infect and replicate in cells having an activated Ras-pathway.

An "interferon sensitive virus" is a virus which does not replicate in or kill normal cells in the presence of interferon. A normal cell is a cell which is not neoplastic as defined above. To test whether a virus is interferon sensitive, a culture of normal cells may be incubated with the virus in the presence of varying concentrations of interferon, and the survival rate of the cells is determined according to well-known methods in the art. A virus is interferon sensitive if less than 20%, preferably less than 10%, of the normal cells is killed at a high concentration of interferon (e.g. 100 units per ml).

"Resistance" of cells to viral infection means that infection of the cells with the virus does not result in significant viral production or yield.

A "viral oncolysate" is a composition prepared by treating tumor cells with an oncolytic virus in vitro, which composition is subsequently administered to a tumor patient with the same kind of tumor in order to induce immunity in the tumor patient against this tumor. As such, viral oncolysates are essentially virus-modified cancer cell membranes.

As used herein, a "transplant recipient" is a mammal which receives a transplantation of cellular compositions. Preferably the recipient is a human, and more preferably the recipient is a human who is receiving transplantation in the treatment of cancer.

Method

The present invention relates to the use of a virus to selectively remove neoplastic cells from mixed cellular compositions which are suspected of containing neoplastic cells. A variety of viruses may be used in this method, each one of which is selective for a neoplasm or a group of neoplasia. Although reovirus is used as an example below, a person of ordinary skill in the art can follow the instructions herein and apply the method to purge any mixed cellular composition by using viruses other than reovirus.

1. Reovirus

We recently discovered that reovirus selectively lyses ras activated neoplastic cells in vitro, in vivo and ex vivo (Coffey et al., 1998; WO 99/08692). Normally, cells are not susceptible to reovirus infection. However, if the ras pathway is activated, reovirus can successfully replicate in the cells and eventually results in lysis of the host cells. For example, when reovirus-resistant NIH 3T3 cells were transformed with activated Ras or Sos, a protein which activates RaS, reovirus infection was enhanced (Strong et al., 1998). Similarly, mouse fibroblasts that are resistant to reovirus infection became susceptible after transfection with the EGF receptor gene or the v-erbB oncogene (Strong et al., 1993; Strong et al., 1996).

Without being limited to a theory, it seems that reovirus replication is regulated at the translational level (Strong et al., 1998; Norman et al., 2000). In untransformed NIH 3T3 cells, early viral transcripts activate the double-stranded RNA-activated protein kinase (PKR), which inhibits translation, thereby inhibiting viral replication. Activated Ras (or an activated element of the ras pathway) presumably inhibits or reverses PKR activation. Therefore, viral protein synthesis proceeds, viral particles are made, and the cells are eventually lysed.

The ras oncogene accounts for a large number of tumors. Activating mutations of the ras gene itself occur in about 30% of all human tumors (Bos, J. L., 1989), primarily in pancreatic (90%), sporadic colorectal (50%) and lung (40%) carcinomas, and myeloid leukemia (30%). Activation of the factors upstream or downstream of ras in the ras pathway is also associated with tumors. For example, overexpression of HER2/Neu/ErbB2 or the epidermal growth factor (EGF) receptor is common in breast cancer (25-30%), and overexpression of platelet-derived growth factor (PDGF) receptor or EGF receptor is prevalent in gliomas and glioblastomas (40-50%). EGF receptor and PDGF receptor are both known to activate ras upon binding to their respective ligand, and v-erbB encodes a constitutively activated receptor lacking the extracellular domain.

We first determined the ability of reovirus to kill cancer cells. Reovirus efficiently caused oncolysis of three breast cancer model systems, MCF7, SKBR3 and HTB 132, by inducing apoptosis in the infected cells (Example 1). Thus, reovirus treatment resulted in a marked decrease in viability of MCF7, SKBR3 and HTB 132 cells, while controls treated with no virus or dead virus grew normally (FIGS. 1A-1D).

The decrease in viability was accompanied by characteristics which are associated with apoptosis, such as DNA fragmentation, annexin V or APO 2.7 staining positivity (FIGS. 2A-2G) and cytopathic effects, such as cell membrane blebbing, nuclear condensation and chromatin condensation observed under the microscope.

Since reovirus infection is usually blocked at the translational level in normal cells but not in ras-mediated neoplastic cells, we examined the extent of protein synthesis in reovirus treated MCF7 cells and CD34$^+$ stem cells (Example 2). Indeed, viral proteins were synthesized in the reovirus infected cancer cell line, but not in CD34$^+$ stem cells which were also treated with reovirus (data not shown). This result suggests that it will be safe to treat hematopoietic stem cells with reovirus, since reoviral proteins were not synthesized in reovirus treated stem cells and cellular protein synthesis proceeded normally. To confirm this point, viability of the reovirus treated CD34$^+$ cells was determined at various time points after reovirus treatment (Example 3). Cell numbers in populations treated with live reovirus or no virus were similar after each time point (FIG. 3A), indicating that CD34$^+$ cells are not susceptible to reovirus infection.

Figure 3B:
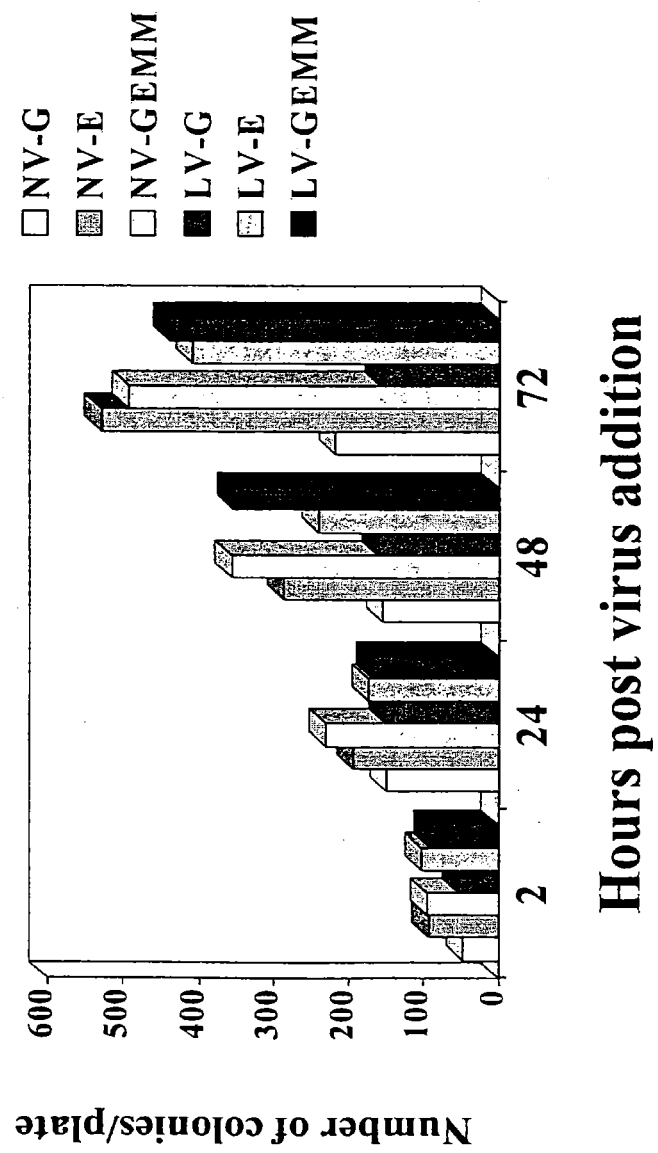
FIG. 3B shows the effect of reovirus on long-term stem cell culture. Stem cells were infected with reovirus and incubated for 2, 24, 48 or 72 hours, respectively, then the cells were diluted and cultured for 14 days to allow individual colonies to form. The number of each kind of colony, granulocytes (G), erythroids (E) or granulocyte erythroid macrophage megakaryocyte (GEMM), was then determined for cells infected with no virus (NV) or live virus (LV), respectively. For example, NV-G stands for the granulocyte colonies derived from cells which were treated with no virus, and LV-G stands for those derived from cells which were treated with live reovirus.

In order for reovirus to be useful in purging hematopoietic stem cell in high dose chemotherapy treatments, it is essential that the reovirus treatment does not alter the ability of stem cells to differentiate into each and every hematopoietic lineage to reconstitute the whole hematopoietic system. Therefore, long term effect of reovirus treatment was assessed (Example 3). CD34$^+$ cells treated with either no virus or live virus showed essentially no difference in their ability to differentiate into granulocytes, erythroids, or granulocyte erythroid macrophage megakaryocytes even after 72 hours of reovirus treatment (FIG. 3B). The ratio between these three lineages also remained the same after this prolonged treatment. Accordingly, reovirus treatment neither killed CD34$^+$ cells nor changed the potential of them to reconstitute the hematopoietic system.

Furthermore, reovirus is capable of purging a mixed cellular composition, as demonstrated by the selective killing of MCF7, SKBR3 or HTB 132 cells in a mixture of cancer cells and apheresis product which contained CD34$^+$ stem cells (Example 4). By measuring CD34 and cytokeratin, a marker specific for epithelial cells such as MCF7, SKBR3 or HTB 132, it was shown that reovirus essentially eliminated the cancer cells from the mixed cellular composition (FIGS. 4A-4C) while leaving the stem cells intact. Therefore, reovirus treatment is an efficient method to purge neoplastic cells from hematopoietic stem cell compositions.

Accordingly, in an embodiment of this invention, stem cell-containing autografts are treated with reovirus prior to transplantation to remove the contaminating or spontaneous ras-activated neoplastic cells. This increases the efficacy of the high dose chemotherapy/autologous hematopoietic stem cell transplantation treatment. Of particular interest will be the treatment of Hodgkin's disease, multiple myeloma, non-Hodgkin's lymphoma, acute myelogenous leukemia, germ cell (testicular) cancers, brain tumors, and breast tumors, since high dose chemotherapy and autologous stem cell transplantation have been performed efficiently in patients with these tumors. However, it is contemplated that the present method will be useful in other cancers as well to remove any ras-mediated neoplastic cells, since activation of the ras pathway may occur in any cell or tissue type.

Hematopoietic progenitor stem cells can be obtained from the bone marrow of the patient in advance of treatment. Alternatively, in a cancer patient who has been receiving traditional, non-high dose chemotherapy, many stem cells typically appear in the peripheral blood with or without colony stimulating factor priming. Therefore, hematopoietic progenitor stem cell can be obtained from the blood as apheresis product, which can be stored for a long time before being transplanted. The present invention can be applied to stem cell-containing autografts which are harvested from any tissue source, including bone marrow and blood.

In addition to hematopoietic stem cells, the present invention can be broadly applied to remove ras-activated neoplastic cells from many other cellular compositions. For example, reovirus can be used as a routine practice to "clean up" (remove ras-activated neoplastic cells from) any tissue or organ transplant. Application of the present invention is not limited by cell or tissue type because as discussed above, the receptor for reovirus is ubiquitous, and the mechanism in normal cells to inhibit reovirus replication, PKR, is also ubiquitous. Therefore, any cell may become a ras-activated neoplastic cell and become susceptible to reovirus infection. Of particular interest will be the use of the claimed methods to clean up whole blood or any portion thereof for a subsequent transfusion. Similarly, tissue or organ transplantation has become increasingly common, and it will be beneficial if the transplant can be treated to remove ras-activated neoplastic cells before transplantation. Liver, kidney, heart, cornea, skin graft, pancreatic islet cells, bone marrow or any portions thereof are just a few examples of the tissues or organs to which this invention can be applied.

The tissue or organ can be autologous, allogeneic or xenogeneic. The tissue or organ may also be derived from a transgenic animal, be a tissue/organ which is developed in vitro from stem cells, or be expanded ex vivo. The tissue or organ to be treated with reovirus can be from an embryonic or adult origin. For example, embryonic neuronal cells can be treated before being transplanted into an Alzheimer's patient. Similarly, the invention can be used to treat semen or donor eggs ex vivo.

Application of the present invention is not limited to transplants. Rather, any cellular compositions can be "cleaned up" with reovirus for any purpose. Thus, all the examples described above are applicable even if the tissue or organ is not meant for transplantation.

Cell lines may also be treated routinely to safeguard against spontaneous or contaminating ras-activated neoplastic cells. Again, any cell line will be a good candidate for this method except, of course, a cell line transformed by means of activation of the ras pathway.

Recently, many laboratories have been attempting to establish serially transplantable xenografts of human prostate cancer tissue inoculated into immune-compromised mice. However, contamination with mouse cancer cells often occurs during the serial passage of the xenografts and these calls can eventually outgrow the human prostate cancer cells (Gao et al., 1999). The present invention will be a simple solution to this problem if the contaminating cancer is ras-mediated and the xenograft is not.

The present invention is distinct from a method of preparing viral oncolysates. Tumor cells are often poor inducers of immune response and can thus escape the attack of the immune system. Viral oncolysates, essentially virus-modified tumor cell membranes, are used in an approach to enhance the immunogenicity of tumor cells. To prepare viral oncolysates, tumor cells are removed from a subject bearing the tumor, and infected with a virus which lyses the tumor cells. The resulting substance is then administered to a subject bearing the tumor, and immunity is often induced against the uninfected tumor cells. The mechanism whereby virus infection of tumor cells induces immunity to uninfected tumor cells is unknown, but virus xenogenization of tumor cells may be involved (Steele, 2000).

Oncolysates of influenza virus-infected melanoma, vulvar carcinoma and ovarian carcinoma, as well as newcastle disease virus infected colon carcinoma oncolysates and vaccinia virus oncolysates have all been used against various tumors. For example, a melanoma patient received oncolysates after surgical excision of the tumor. The viral oncolysate was administered weekly to week 4, every 2 weeks to week 52, every 3 weeks to week 120, and every 6 weeks to week 160. In another clinical case, the administration schedule of autologous NDV oncolysate against colorectal cancer was initiated 2 weeks after surgery and repeated 5 times at 2-week intervals, followed by one boost 3 months later (Nemunaitis, 1999). The studies showed a clinical response in some patients or generation of active immunity against tumor antigens (Steele, 2000).

The present invention is distinct from viral oncolysates in that it is not related to virus-modified tumor cells. In contrast to viral oncolysates, the lysed neoplastic cells can be, and preferably are, removed from the virus-treated cellular composition without affecting the efficacy of the present invention. Furthermore, viral oncolysates are prepared using mostly tumor cells, whereas the mixed cellular composition in the present invention preferably contains less than 60% neoplastic cells, more preferably less than 40%, still more preferably less than 20%, and most preferably less than 10% neoplastic cells.

2. Other Viruses which Selectively Kill Ras-Activated Neoplastic Cells

Normally, when virus enters a cell, double stranded RNA Kinase (PKR) is activated and blocks protein synthesis, and the virus can not replicate in this cell. Some viruses have developed a system to inhibit PKR and facilitate viral protein synthesis as well as viral replication. For example, adenovirus makes a large amount of a small RNA, VA1 RNA. VA1 RNA has extensive secondary structures and binds to PKR in competition with the double stranded RNA (dsRNA) which normally activates PKR. Since it requires a minimum length of dsRNA to activate PKR, VA1 RNA does not activate PKR. Instead, it sequesters PKR by virtue of its large amount. Consequently, protein synthesis is not blocked and adenovirus can replicate in the cell.

Vaccinia virus encodes two gene products, K3L and E3L, which down-regulate PKR with different mechanisms. The K3L gene product has limited homology with the N-terminal region of eIF-2α, the natural substrate of PKR, and may act as a pseudosubstrate for PKR. The E3L gene product is a dsRNA-binding protein and apparently functions by sequestering activator dsRNAs.

Similarly, herpes simplex virus (HSV) gene $_{\gamma 1}$34.5 encodes the gene product infected-cell protein 34.5 (ICP34.5) that can prevent the antiviral effects exerted by PKR. The parapoxvirus orf virus encodes the gene OV20.0L that is involved in blocking PKR activity. Thus, these viruses can successfully infect cells without being inhibited by PKR.

As discussed above, ras-activated neoplastic cells are not subject to protein synthesis inhibition by PKR, because ras inactivates PKR. These cells are therefore susceptible to viral infection even if the virus does not have a PKR inhibitory system. Accordingly, if the PKR inhibitors in adenovirus, vaccinia virus, herpex simplex virus or parapoxvirus orf virus is mutated so as not to block PKR function anymore, the resulting viruses do not infect normal cells due to protein synthesis inhibition by PKR, but they replicate in ras-activated neoplastic cells which lack PKR activities.

Accordingly, the present invention provides a method to remove ras-activated neoplastic cells from a mixed cellular composition by using adenovirus, vaccinia virus, herpes simplex virus or parapoxvirus orf virus which is modified or mutated such that it does not inhibit PKR function. The modified or mutated virus selectively replicate in ras-activated neoplastic cells while normal cells are resistant. Preferably the adenovirus is mutated in the VA1 region, the vaccinia virus is mutated in the K3L and/or E3L region, the herpes simplex virus is mutated in the $_{\gamma 1}$34.5 gene, and the parapoxvirus orf virus is mutated in the OV20.0L gene in this embodiment.

The viruses can be modified or mutated according to the known structure-function relationship of the viral PKR inhibitors. For example, since the amino terminal region of E3 protein interacts with the carboxy-terminal region domain of PKR, deletion or point mutation of this domain prevents anti-PKR function (Chang et al., 1992, 1993, 1995; Sharp et al., 1998; Romano et al., 1998). The K3L gene of vaccinia virus encodes pK3, a pseudosubstrate of PKR. There is a loss-of-function mutation within K3L. By either truncating or by placing point mutations within the C-terminal portion of K3L protein, homologous to residues 79 to 83 in eIF-2α abolish PKR inhibitory activity (Kawagishi-Kobayashi et al., 1997).

3. Viruses Carrying Tumor Suppressor Genes or Tumor Suppressor Related Genes

In another aspect of this invention, the virus selectively kills neoplastic cells by carrying a tumor suppressor gene. For example, p53 is a cellular tumor suppressor which inhibits uncontrolled proliferation of normal cells. However, approximate half of all tumors have a functionally impaired p53 and proliferate in an uncontrolled manner. Therefore, a virus which expresses the wild type p53 gene can selectively kill the neoplastic cells which become neoplastic due to inactivation of the p53 gene product. Such a virus has been constructed and shown to induce apoptosis in cancer cells that express mutant p53 (Blagosklonny et al., 1996).

A similar approach involves viral inhibitors of tumor suppressors. For example, certain adenovirus, SV40 and human papilloma virus include proteins which inactivate p53, thereby allowing their own replication (Nemunaitis 1999). For adenovirus serotype 5, this protein is a 55 Kd protein encoded by the E1B region. If the E1B region encoding this 55 kd protein is deleted, as in the ONYX-015 virus (Bischoff et al, 1996; Heise et al., 2000; WO 94/18992), the 55 kd p53 inhibitor is no longer present. As a result, when ONYX-015 enters a normal cell, p53 functions to suppress cell proliferation as well as viral replication, which relies on the cellular proliferative machinery. Therefore, ONYX-015 does not replicate in normal cells. On the other hand, in neoplastic cells with disrupted p53 function, ONYX-015 can replicate and eventually cause the cell to die. Accordingly, this virus can be used to selectively infect and remove p53-deficient neoplastic cells from a mixed cellular composition. A person of ordinary skill in the art can also mutate and disrupt the p53 inhibitor gene in adenovirus 5 or other viruses according to established techniques, and the resulting viruses are useful in the present method to remove neoplastic cells from mixed cellular compositions.

Another example is the Delta24 virus which is a mutant adenovirus carrying a 24 base pair deletion in the E1A region (Fueyo et al., 2000). This region is responsible for binding to the cellular tumor suppressor Rb and inhibiting Rb function, thereby allowing the cellular proliferative machinery, and hence virus replication, to proceed in an uncontrolled fashion. Delta24 has a deletion in the Rb binding region and does not bind to Rb. Therefore, replication of the mutant virus is inhibited by Rb in a normal cell. However, if Rb is inactivated and the cell becomes neoplastic, Delta24 is no longer inhibited. Instead, the mutant virus replicates efficiently and lyses the Rb-deficient cell. Again, this virus is selective for neoplastic cells and can be used to purge mixed cellular compositions and remove Rb-deficient cells.

4. Other Viruses

Vesicular stomatitis virus (VSV) selectively kills neoplastic cells in the presence of interferon. Interferons are circulating factors which bind to cell surface receptors which ultimately lead to both an antiviral response and an induction of growth inhibitory and/or apoptotic signals in the target cells. Although interferons can theoretically be used to inhibit proliferation of tumor cells, this attempt has not been very successful because of tumor-specific mutations of members of the interferon pathway.

However, by disrupting the interferon pathway to avoid growth inhibition exerted by interferon, tumor cells may simultaneously compromise their anti-viral response. Indeed, it has been shown that VSV, an enveloped, negative-sense RNA virus rapidly replicated in and killed a variety of human tumor cell lines in the presence of interferon, while normal human primary cell cultures were apparently protected by interferon. An intratumoral injection of VSV also reduced tumor burden of nude mice bearing subcutaneous human melanoma xenografts (Stojdl et al., 2000).

Accordingly, in another embodiment of the present invention, VSV is used to remove neoplastic cells from a mixed cellular composition in the presence of interferon. Moreover, it is contemplated that this aspect of the invention be applied to any other interferon-sensitive virus (WO 99/18799), namely a virus which does not replicate in a normal cell in the presence of interferons. Such a virus may be identified by growing a culture of normal cells, contacting the culture with the virus of interest in the presence of varying concentrations of interferons, then determining the percentage of cell killing after a period of incubation. Preferably, less than 20% normal cells is killed and more preferably, less than 10% is killed.

It is also possible to take advantage of the fact that some neoplastic cells express high levels of an enzyme and construct a virus which is dependent on this enzyme. For example, ribonucleotide reductase is abundant in liver metastases but scarce in normal liver. Therefore, a herpes simplex virus 1 (HSV-1) mutant which is defective in ribonucleotide reductase expression, hrR3, was shown to replicate in colon carcinoma cells but not normal liver cells (Yoon et al., 2000).

In addition to the viruses discussed above, a variety of other viruses have been associated with tumor killing, although the underlying mechanism is not always clear. Newcastle disease virus (NDV) replicates preferentially in malignant cells, and the most commonly used strain is 73-T (Reichard et al., 1992; Zorn et al, 1994; Bar-Eli et al, 1996). Clinical antitumor activities wherein NDV reduced tumor burden after intratumor inoculation were also observed in a variety of tumors, including cervical, colorectal, pancreas, gastric, melanoma and renal cancer (WO 94/25627; Nemunaitis, 1999). Therefore, NDV can be used to remove neoplastic cells from a mixed cellular composition.

Moreover, vaccinia virus propagated in several malignant tumor cell lines. Encephalitis virus was shown to have an oncolytic effect in a mouse sarcoma tumor, but attenuation may be required to reduce its infectivity in normal cells. Tumor regression have been described in tumor patients infected with herpes zoster, hepatitis virus, influenza, varicella, and measles virus (for a review, see Nemunaitis, 1999).

According to the methods disclosed herein and techniques well known in the art, a skilled artisan can test the ability of these or other viruses to selectively kill neoplastic cells in order to decide which virus can be used to remove neoplastic cells from a mixed cellular composition of interest.

4. Removal of Viruses after Virus Treatment

Although the virus used in the present invention does not replicate in normal cells, it may be desired to remove the virus prior to using the virus treated cellular composition. For example, reovirus is not associated with any known disease, but it may be more infectious to cancer patients whose immune systems are weakened due to chemotherapy. Therefore, if reovirus is used to treat a composition comprising hematopoietic stem cells which will subsequently be transplanted to a cancer patient, reovirus can be removed prior to transplantation of the cellular composition.

Accordingly, in another embodiment of this invention, the cellular compositions which have been treated with a virus are frozen in a solution containing DMSO and thawed prior to transplantation. While DMSO is routinely used to freeze and store animal cells, it denatures viruses, thereby removing infectious virus from the stem cell preparation. This reduces the risk that the virus may cause undesired infections when it is introduced into the transplant recipient via stem cell transplantation.

In another embodiment, the virus-treated cell compositions are treated with specific antibodies against the particular virus or a combination of the specific antibodies and complements in order to inactivate or lyse the virus. Alternatively or additionally, specific antibodies which recognize a molecule on the surface of the particular virus may be used to remove the virus particles from the virus-treated cellular composition. Thus, the antibodies are immobilized to a column, beads or any other material or device known in the art, the cellular composition is applied to the immobilzed antibodies, and the part of the composition which does not bind to the antibodies is collected according to a procedure suitable for the particular method of immobilization.

Another method which may be used to remove the virus from virus-treated mixture is to subject the mixture to a gradient which separates cells from the virus, and collect the layer that contains only the cells.

In another embodiment, the transplant recipient is given treatments to stimulate the immune system in order to reduce the risk of virus infection. This treatment may be performed prior to, contemporaneously with, or after the transplantation, but is preferably performed prior to the transplantation. As an alternative treatment or in conjunction with the immune system stimulant, the recipient can be given specific antibodies against the particular virus in order to reduce the risk of virus infection.

Composition

The present invention provides a composition which is prepared by subjecting a mixed cellular composition to virus treatment wherein the virus results in substantial killing of the neoplastic cells contained in this cellular composition. This composition is not a viral oncolysate. A viral oncolysate is the composition resulting from oncolysis of tumor cells by a virus, containing as the active component virus-modified tumor cell membranes. In the present invention, by contrast, the active components in a virus-treated cellular composition are the surviving non-neoplastic cells.

Kit

All the viruses discussed above can be used to purge mixed cellular compositions which may contain neoplastic cells. If desired, it may be determined first which virus or viruses can be used to purge the particular cellular composition. For example, when the mixed cellular composition comprises hematopoietic stem cells obtained from a cancer patient, a biopsy of the cancer can be harvested in advance and tested with different viruses to determine which virus can efficiently kill the cancer cells. The virus can then be used to purge the hematopoietic stem cells.

Alternatively, the mixed cellular composition may be treated with a cocktail of viruses without first determining the efficacy of each virus. Accordingly, this invention provides a kit comprising a group of viruses with different or overlapping specificities. For example, the kit may contain reovirus for ras-activated neoplastic cells, a p53 expressing virus for p53 deficient neoplastic cells, Delta24 for Rb deficient neoplastic cells, Onyx-015 for p53 deficient neoplastic cells, vesicular stomatitis virus for interferon resistant neoplastic cells, or subsets thereof.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

° C.=degree Celsius
hr=hour
min=minute
μM=micromolar
mM=millimolar
M=molar
ml=milliliter
μl=microliter
mg=milligram
μg=microgram
PAGE=polyacrylamide gel electrophoresis
rpm=revolutions per minute
FBS=fetal bovine serum
DTT=dithiothrietol
SDS=sodium dodecyl sulfate
PBS=phosphate buffered saline
DMEM=Dulbecco's modified Eagle's medium
α-MEM=α-modified Eagle's medium
β-ME=β-mercaptoethanol
MOI=multiplicity of infection
PFU=plaque forming units
PKR=double-stranded RNA activated protein kinase
EGF=epidermal growth factor
PDGF=platelet derived growth factor
DMSO=dimethylsulfoxide
CPE=cytopathic effect
GCSF=granulocyte colony stimulating factor Example 1

Reovirus Induced Oncolysis and Apoptosis in Breast Cancer Cells

To determine the effect of reovirus on the viability of neoplastic cells, we first used three breast cancer model systems, MCF7 (ATCC number HTB-22), SKBR3 (ATCC number HTB-30) and MDA MB 468 (ATCC number HTB 132). Cells of each cell line were grown to 50-60% confluency and infected with reovirus serotype 3, strain Dearing, at a multiplicity of infection of 40. Reovirus was obtained and maintained as described in U.S. Pat. No. 6,136,307. Reovirus infected and non-infected cells were harvested at 0, 24, 48 and 72 hours after infection and the viability was determined.

The results are shown in FIGS. 1A-1D. Viable cell count in reovirus-infected MCF7 (FIG. 1A), SKBR3 (FIG. 1B) or MDA MB 468 cells (FIG. 1C) dropped significantly after the infection, while the cells infected with dead virus or no virus proliferated as expected. Reovirus treatment caused MCF7 (FIG. 1D) and SKBR3 viability to drop from 93% to 16% by 72 hours after infection. In MDA MB 468 cells, virus treated intact cell numbers dropped to 12.7%, 8.8% and 3.6% of the original cell counts, respectively, at 24, 48 and 72 hours after infection. Thus, reovirus caused oncolysis efficiently in all three kinds of cancer cells.

The cells died by apoptosis. Typical apoptotic markers such as CPE, Annexin-V and DNA laddering could be observed in a time course parallel to the decrease of viability. FIGS. 2A-2G show the percentage of DNA fragmentation (2A-2C), Annexin V staining (2D) or APO2.7$^+$ cells (2E-2G) at various time points after reovirus infection. The reovirus treated cells exhibited all signs of apoptosis at a dramatic level compared to the no virus or dead virus controls, demonstrating that reovirus induced apoptosis in all of these three cell lines. Apoptosis in the controls seemed to increase slowly with time as well, probably because cells began to die when they had grown too densely.

Example 2

Reovirus Selectively Inhibited Protein Synthesis in Cancer Cells but not CD34$^+$ Stem Cells For further proof of selective viral infection of cancer cells, $^{35}$S labeling/SDS/PAGE of viral proteins was undertaken. Viral protein synthesis was evident after 1-2 days in MCF7 cells infected with reovirus, while cellular protein synthesis decreased at the same time, indicating that reovirus had taken over the cellular machinery. At 4 days after infection, no protein synthesis could be detected anymore, suggesting that all the cells had been killed. In the control experiments where cells were infected with dead reovirus or no virus, there was no viral protein synthesis, whereas cellular protein synthesis was at the normal level. In contrast, $^{35}$S labeling of CD34$^+$ stem cells in the presence or absence of reovirus showed no viral protein synthesis up to 72 hours after the addition of virus. Therefore, reovirus selectively infect MCF7 cells but not CD34$^4$ stem cells.

Example 3

Reovirus Treatment Neither Inhibited Cell Proliferation Nor Altered Differentiation Potential of CD34$^+$ Cells Consistent with the protein synthesis results, viable cell count indicated that reovirus treatment did not decrease the number of viable cells in CD34$^+$ cells (FIG. 3A) as compared to the no virus control.

While the number of CD34$^+$ cells was unaffected by reovirus infection, there remained the question whether reovirus changed the potential of CD34$^+$ stem cells to differentiate into all the hematopoietic lineages in the appropriate proportion. If this was the case, reovirus treated stem cells would not be a good candidate for the reconstitution of the whole hematopoietic system. To investigate this possibility, CD34$^+$ cells were incubated with reovirus for 2, 24, 48 or 72 hours, respectively. The reovirus was then removed and the cells were diluted and cultured in fresh media for 14 days to allow colonies to form. Each colony was examined to determine if it belongs to the granulocyte, erythroid, or granulocyte erythroid macrophage megakaryocyte lineage. As shown in FIG. 3B, stem cells treated with live virus (LV) yielded similar numbers of granulocutes (G), erythrocytes (E) or granulocyte erythroid macrophage megakaryocytes (GEMM) as the no virus (NV) control. Therefore, reovirus treatment did not change the differentiation potential of $CD34^+$ cells.

Example 4

Reovirus Selectively Removed Cancer Cells from a Mixed Cellular Composition

Figure 4A:
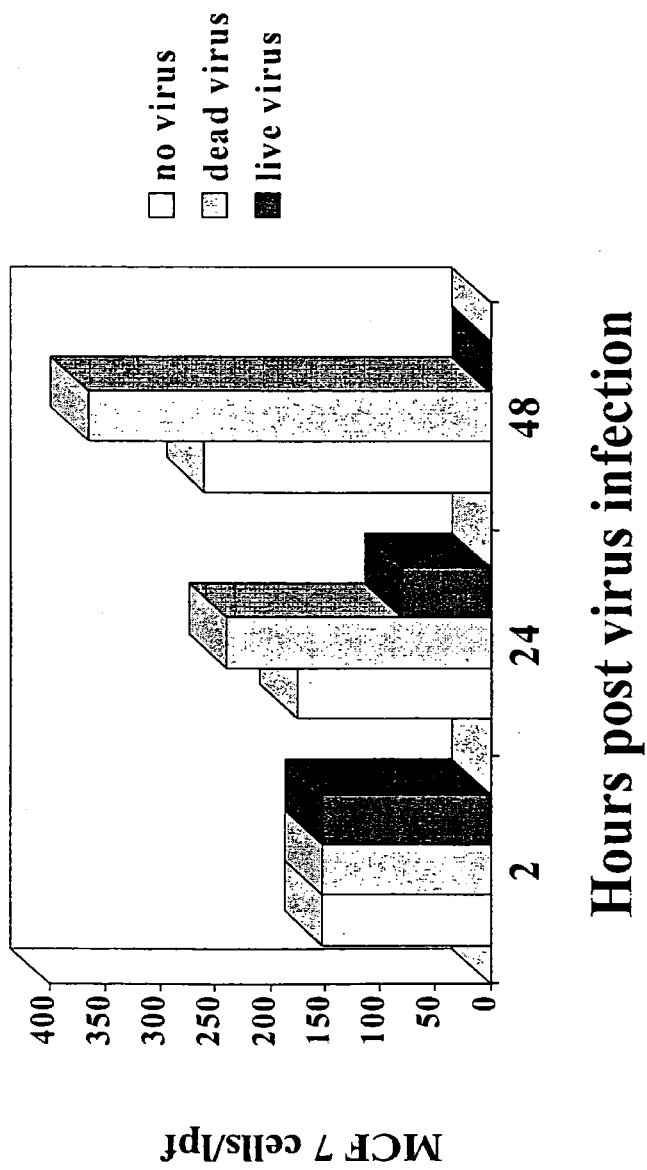
FIGS. 4A-4C show the purging effects of reovirus on mixtures of apheresis product with MCF7, MDA MB 468 or SKBR3 cells, respectively.
Figure 4B:
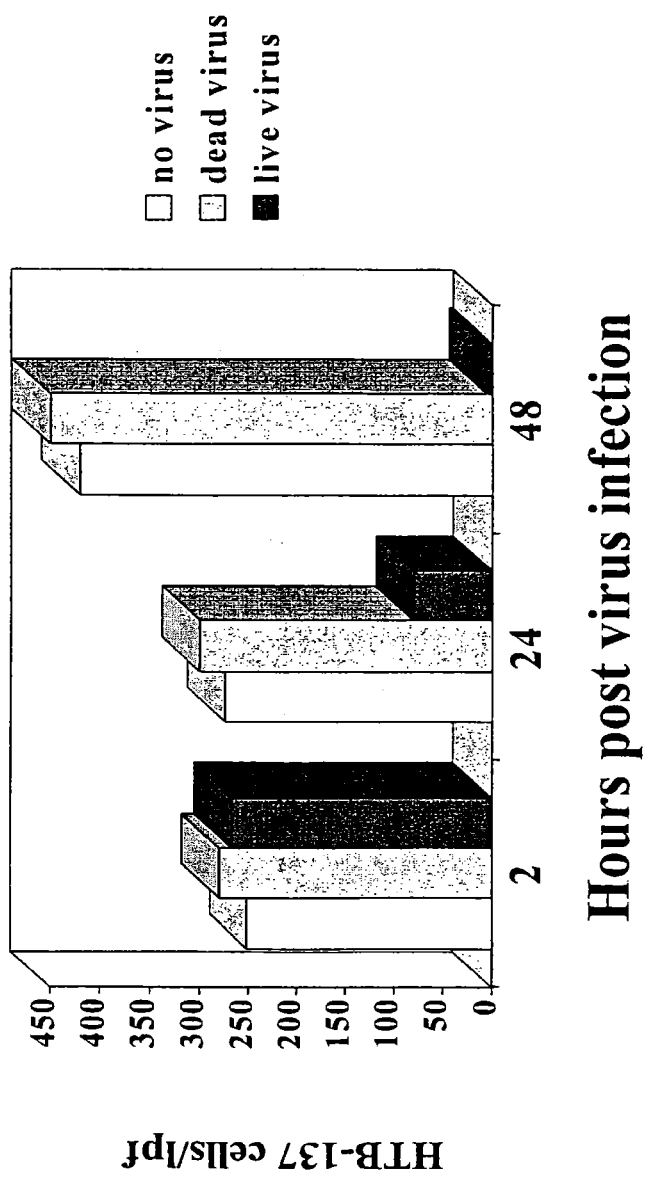
Figure 4C:
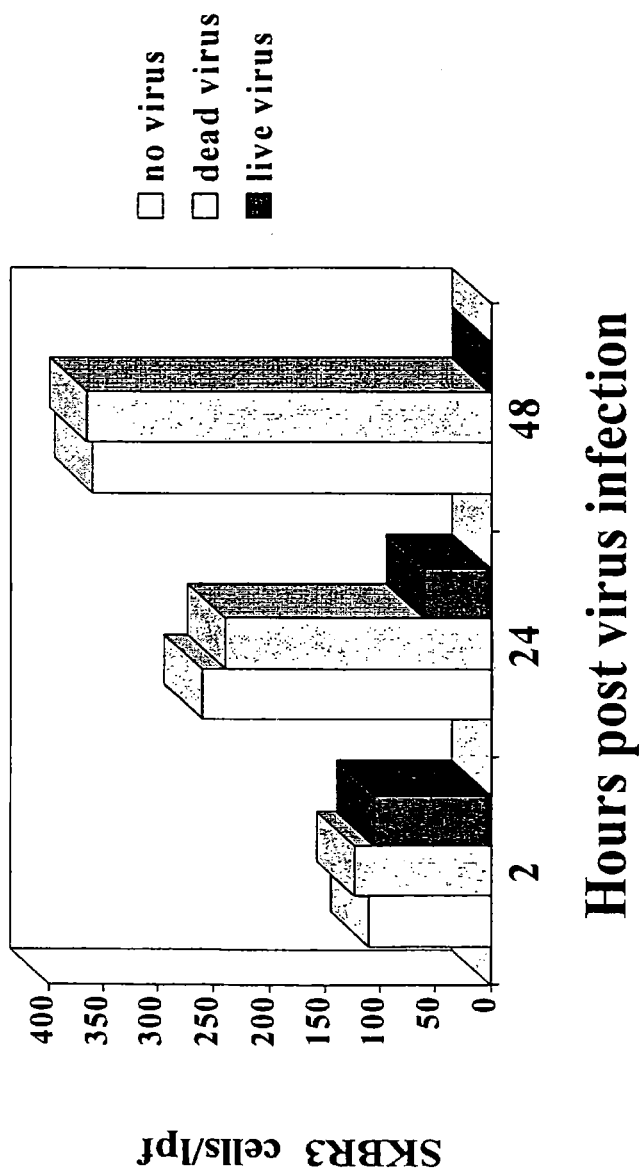

Neoplastic cells were mixed with apheresis product and subjected to reovirus infection to investigate if reovirus can selectively remove neoplastic cells from the mixed cellular composition. Apheresis product was prepared according to a procedure previously described (Stewart et al., 1999; Duggan et al., 2000). When admixtures of apheresis product (90%) and MCF7 (10%) were treated with reovirus and tested daily for cell count and viability, there was a 100-fold depletion in the numbers of cytokeratin-positive MCF7 cells while the $CD34^+$ stem cells remained intact and viable. FIGS. 4A-4C show the purging effect of reovirus to mixtures of apheresis product with MCF7, SKBR3 or MDA MB 468 cells. These results demonstrate that reovirus can selectively kill neoplastic cells in a cell mixture and leave the stem cells intact.

We claim:

1. A method of selectively removing neoplastic cells from a mixed cellular composition, wherein the composition is located outside of a living organism, the method comprising the steps of:
   (a) selecting a mixed cellular composition comprising ras-activated neoplastic cells;
   (b) contacting the mixed cellular composition with a replication-competent oncolytic virus under conditions that result in substantial killing of the ras-actived neoplastic cells, wherein the replication-competent oncolytic virus is a vaccinia virus; and
   (c) collecting the virus-treated cellular composition.

2. The method of claim 1, wherein the replication-competent oncolytic vaccinia virus is mutated or modified such that the virus does not produce a gene product that inhibits double stranded RNA kinase (PKR).

3. The method of claim 1, wherein the replication-competent oncolytic virus is selected from the group consisting of vaccinia viruses having a mutation in the K3L or E3L genes.

4. The method of claim 1, wherein the mixed cellular composition comprises hematopoietic stem cells.

5. The method of claim 1, wherein the mixed cellular composition comprises CD34+ stem cells.

6. The method of claim 5, further comprising the step of selecting CD34+ cells from the mixed cellular composition prior to step (b).

7. The method of claim 4, wherein the hematopoietic stem cells are harvested from blood.

8. The method of claim 4, wherein the hematopoietic stem cells are harvested from bone marrow.

9. The method of claim 1, wherein the mixed cellular composition comprises a tissue, an organ or any portion of a tissue or organ.

10. The method of claim 9, wherein the tissue or organ is selected from the group consisting of liver, kidney, heart, cornea, skin, and lung.

11. The method of claim 1, wherein the mixed cellular composition comprises pancreatic islet cells.

12. The method of claim 1, wherein the mixed cellular composition is whole blood.

13. The method of claim 1, wherein the mixed cellular composition comprises cultured cells.

14. The method of claim 1, wherein the mixed cellular composition comprises semen or eggs.

15. The method of claim 1, further comprising the step of removing the replication-competent oncolytic virus from the virus-treated cellular composition.

16. The method of claim 1, further comprising the step of freezing and storing the virus-treated composition in a solution containing DMSO.

17. The method of claim 15, wherein the step of removing the replication-competent oncolytic virus from the virus-treated composition comprises contacting the virus-treated composition with an anti-virus antibody.

18. The method of claim 15, wherein the step of removing the replication-competent oncolytic virus from the virus-treated composition comprises contacting the virus-treated composition with anti-virus antibodies and complement.

19. The method of claim 1, further comprising subjecting the virus-treated cellular composition to a gradient that separates the cells of the cellular composition from the replication-competent oncolytic virus.

20. The method of claim 19, further comprising collecting the cells of the cellular composition.

21. The method of claim 1, further comprising transplanting the virus treated cellular composition into a mammal.

22. A method of preparing a cellular transplant with a reduced amount of ras-activated neoplastic cells, said method comprising the steps of:
   (a) providing a mixed cellular composition which comprises ras-activated neoplastic cells;
   (b) contacting the mixed cellular composition with a replication competent virus under conditions which result in substantial killing of the ras-activated neoplastic cells so as to selectively remove the ras-activated neoplastic cells from the composition, wherein the replication competent virus is vaccinia virus; and
   (c) removing the virus from the virus treated cellular composition.

23. The method of claim 22, wherein the replication-competent oncolytic virus is vaccinia viruses having a mutation in the K3L or E3L genes.

24. The method of claim 22, wherein the mixed cellular composition comprises hematopoietic stem cells.

25. The method of claim 22, wherein the hematopoietic stem cells have been harvested from bone marrow.

26. The method of claim 22, wherein the hematopoietic stem cells have been harvested from blood.

27. The method of claim 22, wherein the mixed cellular composition comprises a tissue, an organ or any portion of a tissue or an organ.

28. The method of claim 27, wherein the tissue or organ is selected from the group consisting of liver, heart, kidney, cornea, skin, lung, pancreatic islet cells, and whole blood.

29. The method of claim 22, wherein the mixed cellular composition comprises cultured cells, semen and eggs.

30. The method of claim 22, further comprising storing the composition of step (c) in a solution containing DMSO before step (d).

31. The method of claim 22, wherein the replication competent virus is mutated or modified such that the virus does not produce a gene product which inhibits double stranded RNA kinase (PKR).

32. The method of claim 22 wherein step (c) is performed by using an antibody or gradient.

33. The method of claim 22, wherein the replication competent virus is mutated or modified such that the virus does not produce a gene product which inhibits double stranded RNA kinase (PKR).

34. A method of transplanting into a mammal a cellular composition with a reduced amount of ras-activated neoplastic cells, wherein the cellular composition is prepared by the method of claim 22.

35. The method of claim 34, wherein the mammal is a human.

36. The method of claim 34, wherein the mammal has cancer.

37. The method of claim 34, wherein the transplantation is an autologous transplantation.

38. The method of claim 34, wherein the transplantation is an allogeneic transplantation.

39. A method of preparing a cellular transplant with a reduced amount of ras-activated neoplastic cells, said method comprising the steps of:
(a) providing a mixed cellular composition which comprises ras-activated neoplastic cells;
(b) contacting the mixed cellular composition with a replication competent virus under conditions which result in substantial killing of the ras-activated neoplastic cells so as to selectively remove the ras-activated neoplastic cells from the composition, wherein the replication competent virus is a vaccinia virus having a mutation in the K3L or E3L gene;
(c) removing the virus from the virus treated cellular composition; and
(d) transplanting the resulting composition into the mammal, wherein step (c) is performed in the absence of DMSO.

40. The method of claim 39, wherein the mixed cellular composition comprises hematopoietic stem cells.

41. The method of claim 39, wherein the hematopoietic stem cells have been harvested from bone marrow.

42. The method of claim 39, wherein the hematopoietic stem cells have been harvested from blood.

43. The method of claim 39, wherein the transplantation is an autologous transplantation.

44. The method of claim 39, wherein the transplantation is an allogeneic transplantation.

* * * * *